United States Patent
Baeurele

(10) Patent No.: US 12,087,448 B2
(45) Date of Patent: *Sep. 10, 2024

(54) REPRESENTATION OF SYMPTOM ALLEVIATION

(71) Applicant: COGNIFISENSE, INC., Sunnyvale, CA (US)

(72) Inventor: Tassilo Baeurele, Sunnyvale, CA (US)

(73) Assignee: COGNIFISENSE, INC., Sunnyvale, CA (US)

( * ) Notice: Subject to any disclaimer, the term of this patent is extended or adjusted under 35 U.S.C. 154(b) by 614 days.

This patent is subject to a terminal disclaimer.

(21) Appl. No.: 17/333,179

(22) Filed: May 28, 2021

(65) Prior Publication Data
US 2021/0296003 A1   Sep. 23, 2021

Related U.S. Application Data

(63) Continuation-in-part of application No. 16/267,038, filed on Feb. 4, 2019, now Pat. No. 11,024,430, which
(Continued)

(51) Int. Cl.
*G16H 50/50*   (2018.01)
*G06N 20/00*   (2019.01)
(Continued)

(52) U.S. Cl.
CPC ............ *G16H 50/50* (2018.01); *G06N 20/00* (2019.01); *G16H 20/30* (2018.01); *G16H 40/67* (2018.01); *G16H 70/60* (2018.01)

(58) Field of Classification Search
CPC ........ G16H 50/50; G16H 20/30; G16H 40/67; G16H 70/60; G06N 20/00; G06F 3/167
See application file for complete search history.

(56) References Cited

U.S. PATENT DOCUMENTS 8,930,208 B2   1/2015   Hyde et al.
8,942,817 B2 *   1/2015   Hyde ................... A61B 5/0022
                                                                607/60
(Continued)

FOREIGN PATENT DOCUMENTS

KR   10-2002-0035030 A     5/2002
WO   WO-2005061045 A1 *  7/2005   ......... A61N 1/36014
(Continued)

OTHER PUBLICATIONS

Cavrag et al., Interaction with Virtual Spiders for Eliciting Disgust in the Treatment of Phobias, 2014 IEEE International Symposium on Haptic, Audio and Visual Environments and Games (HAVE). Proceedings, 2014. (Year: 2014).*
(Continued)

*Primary Examiner* — Christopher L Gilligan
(74) *Attorney, Agent, or Firm* — Workman Nydegger

(57) ABSTRACT

Systems and methods are provided for generating dynamic representations of symptoms and symptom alleviation. The system generates a multidimensional sensory environment configured to provide sensory signals associated with a symptom of a user. The multidimensional sensory environment provides visual sensory signals associated with the symptom as well as one or more of audio, tactile, or olfactory signals associated with the symptom.

22 Claims, 11 Drawing Sheets

Related U.S. Application Data is a continuation of application No. 15/980,086, filed on May 15, 2018, now Pat. No. 10,249,391, which is a continuation of application No. PCT/US2016/062348, filed on Nov. 16, 2016.

(60) Provisional application No. 62/255,946, filed on Nov. 16, 2015.

(51) Int. Cl.
*G16H 20/30* (2018.01)
*G16H 40/67* (2018.01)
*G16H 70/60* (2018.01)

(56) References Cited

U.S. PATENT DOCUMENTS

| | | |
|---|---|---|
| 9,198,622 B2 | 12/2015 | Kaleal, III et al. |
| 9,694,155 B2 | 7/2017 | Panova et al. |
| 2006/0161218 A1 | 7/2006 | Danilov |
| 2009/0005649 A1 | 1/2009 | Baird et al. |
| 2011/0184250 A1 | 7/2011 | Schmidt et al. |
| 2011/0213197 A1 | 9/2011 | Robertson et al. |
| 2012/0182291 A1* | 7/2012 | Rawat .............. G06T 17/00 345/419 |
| 2013/0324805 A1 | 12/2013 | Sprague |
| 2014/0078144 A1 | 3/2014 | Berriman et al. |
| 2014/0088990 A1* | 3/2014 | Nawana ............ G16H 40/40 705/2 |
| 2014/0187317 A1 | 7/2014 | Kohler et al. |
| 2014/0344740 A1 | 11/2014 | Kaula et al. |
| 2015/0174362 A1 | 6/2015 | Panova et al. |
| 2015/0309316 A1 | 10/2015 | Osterhout et al. |
| 2015/0324544 A1 | 11/2015 | Maslowski et al. |
| 2016/0005320 A1* | 1/2016 | deCharms ........ G09B 19/00 434/236 |
| 2016/0026253 A1 | 1/2016 | Bradski et al. |

FOREIGN PATENT DOCUMENTS

| | | |
|---|---|---|
| WO | 2011/120121 A1 | 10/2011 |
| WO | 2012/154620 A2 | 11/2012 |

OTHER PUBLICATIONS

Examiner Interview Summary received for U.S. Appl. No. 16/267,038, mailed on Feb. 2, 2021, 3 pages.

Extended European Search Report issued ins PCT/US2016062348 dated Mar. 14, 2019.

Gerardi, et al., Virtual Reality Exposure Therapy Using a Virtual Iraq: Case Report, Apr. 2008, J Trauma Stress, pp. 1-9. (Year: 2008).

International Search Report and Written Opinion issued in PCT/US2016/062348 dated Mar. 24, 2017.

Shiri, et al., A Virtual Reality System Combined with Biofeedback for Treating Pediatric Chronic Headache—A Pilot Study, 2013, Pain Medicine, pp. 621-627. (Year: 2013).

* cited by examiner

302 Create/modify a first digital model for a context, which enables generation of a sensory environment comprising first digital signals.

304 Create/modify a second digital model for a symptom, which enables generation of second sensory signals, and a third digital model for a symptom alleviation process, which enables generation of third sensory signals.

306 Cause generation of the first, second, and third sensory signals, where at least a portion of the second and/or third sensory signals change continuously over time to human perception.

308 Analyze biofeedback to adjust the first, second, or third digital models.

*FIG. 3*

REPRESENTATION OF SYMPTOM ALLEVIATION

CROSS-REFERENCE TO RELATED APPLICATIONS

This application is a continuation-in-part of U.S. patent application Ser. No. 16/267,038, filed Feb. 4, 2019, which is a continuation of U.S. patent application Ser. No. 15/980,086, filed May 15, 2018, now patented as U.S. Pat. No. 10,249,391 with issue date Apr. 2, 2019, which is a continuation of International Patent Application No. PCT/US2016/062348, filed Nov. 16, 2016, which claims the benefit of U.S. Provisional Patent Application No. 62/255,946 filed Nov. 16, 2015, each of which are incorporated herein by reference in their entirety.

BACKGROUND

Suitable management of symptoms (e.g., pain) of adverse health conditions can help patients have better lives. The mind is an integral part of the pain experience in any patient, human or animal. When a patient's perception is influenced, the whole psychology of pain, indeed the whole experience of the pain, can change dramatically, even if the source of the pain itself is not influenced. The same is true for many other symptoms. For example, mirror therapy is shown possessing power of using real visual input to provide significant, lasting relief from pain. Mirror therapy is based on observing a virtual recovery of a missing limb or a recovery of function in an affected body part in a mirror and can lead to a reduction in the perceived pain. Nevertheless, mirror therapy has its limitations. Mirror therapy using a mirror box can be cumbersome, and mirror therapy, in general, is more effective when there is a visual cue for the pain, such as a missing limb. Many types of pain, such as headaches or back pain, don't have a related visible cue.

It would be helpful to have a new paradigm of methods and systems that provide a patient with a virtual, yet realistic and strongly impactful representation of the patient's symptoms and their alleviation, because this would further stimulate the patient's mind to change perception of pain and symptom alleviation.

SUMMARY

The technologies disclosed herein include methods, systems, and storage media for symptom (e.g., pain) management based on multimedia technologies. The disclosed methods and systems create a multidimensional sensory environment, further creating various sensory objects or forms to represent a symptom within the sensory environment. The technologies further allow the user to simulate various health improving schemes through interaction with the sensory representations of the symptom. The technologies allow the user to sense potential effects of the health improvements, leading to a change in psychological perception of the symptom and its improvement. Applications of the technologies can enable pain reduction, support physical therapy of stroke victims or neurodegenerative illness, treat other physical and psychological disorders, and improve other symptoms.

Besides using the disclosed technologies to sense potential health improvement, a patient can learn a behavioral technique for dealing with a health issue. For example, in the use of the technologies for the alleviation of chronic pain due to an irreversible condition, the user can use the technologies to learn how to apply mental coping strategies for perceiving the pain and its broader role in the patient's life.

In one aspect, a method of representing symptoms and symptoms alleviation is provided. The method comprises creating, by one or more processors, a first digital model for generating a sensory environment comprising first sensory signals; causing an output device to execute the first digital model to generate the sensory environment; creating a second digital model for a symptom, wherein the second digital model causes generation of second sensory signals; causing the output device to generate the second sensory signals within the sensory environment based on the second digital model; creating a third digital model of an alleviation or removal of the symptom based on the first or the second digital models, wherein the third digital model causes generation of third sensory signals, and wherein at least a portion of the second sensory signals and/or third sensory signals change continuously over time to human perception; and causing the output device to generate the third sensory signals within the sensory environment based on the third digital model.

In some embodiments, the output device comprises multiple devices and the first sensory signals, second sensory signals, and third sensory signals are individually or collectively sent to one or more of the multiple devices. In some embodiments, the first sensory signals, second sensory signals, or third sensory signals form holographic, virtual-reality, or augmented-reality representations. In some embodiments, the output device produces audio, visual, tactile, or olfactory signals. In some embodiments, the first sensory signals, second sensory signals, or third sensory signals are produced responsive to user input.

In some embodiments, the method further comprises receiving a description of the symptom, wherein creating the second digital model is based on the description. In some embodiments, the description of the symptom comprises one or more of a photo, a video, an animation, a sound, a vibration, or a scent. In some embodiments, the sensory environment includes a user interface for providing a description of the symptom or selecting from a set of predefined descriptions. In some embodiments, the description is for various pain types, including one or more of aching, throbbing, sore, stabbing, shooting, stabbing, cramping, gnawing, splitting, heavy, or burning.

In some embodiments, the second digital model is modified to represent changes in qualities of the symptom, including duration, intensity, frequency, depth, topography, sharpness, or appearance. In some embodiments, the method further comprises modifying the second digital model responsive to user input.

In some embodiments, the sensory environment includes an avatar of a user. In some embodiments, a view of the avatar corresponds to a first-person view or a third-person view for the user. In some embodiments, the avatar switches between the first- and third-person views. In some embodiments, there is no avatar specifically corresponding to the user.

In some embodiments, the method further comprises modifying the first digital model to generate a change to the avatar responsive to user input. In some embodiments, the second or third sensory signals are generated on or within the avatar.

In some embodiments, the method further comprises determining a symptom alleviation method, wherein creation of the third digital model is based on the symptom alleviation method. In some embodiments, the symptom alleviation method includes parameters comprising a duration, intensity, manner, or quality of symptom alleviation.

In some embodiments, the third digital model corresponds to one or more of: a reduction in size of, an increase of a distance from; an evaporation of; a recoloring/discoloration of; a dilution of; a diffusion of; a dissipation of; a relocation of; a reduction in frequency of; a distortion of; a disappearing of; a washing or blowing away of; a removal of; a throwing away of; a silencing of; a slowing of; a melting of; a healing of; a stilling of; or a cooling of the symptom.

In some embodiments, the third digital model corresponds to creating a set of stimuli, which leads the user to experience changes in body self-perception or an out-of-body experience. In some embodiments, the third sensory signals create a sensation within the user of the mind or consciousness of the user leaving the user's body and floating above or beside the user's body, the mind or consciousness moving from one body to another, a part of the body leaving the main body, or one or more symptoms leaving the body.

In another aspect, a method of representing symptom alleviation is provided. The method comprises receiving information regarding alleviating a symptom, including a selection from a plurality of predetermined modes for representing symptom alleviation; generating a digital model for alleviating the symptom based on the received information; and managing a symptom alleviation experience based on the received information. In some embodiments, the plurality of predetermined modes includes a passive mode, an active mode, or a responsive mode, wherein when the selection is the passive mode, the managing includes sending the digital model to an output device and causing the output device to generate sensory signals based on the digital model, wherein when the selection is the active mode, the managing includes receiving user instructions from an input device, and wherein when the selection is the responsive mode, the managing includes receiving biometric data from a sensor device. In some embodiments, when the selection is the active or responsive mode, the managing further includes updating the digital model based on the user instructions or user biofeedback. In some embodiments, the biofeedback includes a heart rate, heart rate variability, breathing, galvanic skin response, brain waves, EEG signals, fMRI signals, or muscle tension.

In some embodiments, the method further comprises receiving a specification of a symptom alleviation method; generating a simplified version of the first, second, or third digital model, and sending the specification and the simplified version to a remote device over a communication network.

In some embodiments, the third digital model includes verbal or visual information for a user, including skills for coping with the symptom or affirmations on the user's power to control or alleviate the symptom.

In another aspect, a system for representing symptoms and symptom alleviation is provided. The system comprises a processor; and a memory operatively coupled to the processor and configured for storing data instructions that, when executed by the processor, cause the system to perform a method, the method comprising: creating a first digital model for generating a sensory environment comprising first sensory signals; causing an output device to execute the first digital model to generate the sensory environment; creating a second digital model for a symptom, wherein the second digital model causes generation of second sensory signals; causing the output device to generate the second sensory signals within the sensory environment based on the second digital model; creating a third digital model of an alleviation or removal of the symptom based on the first or the second digital models, wherein the third digital model causes generation of third sensory signals, and wherein at least a portion of the second sensory signals and/or third sensory signals change continuously over time to human perception; and causing the output device to generate the third sensory signals within the sensory environment based on the third digital model.

In some embodiments, the output device is a head mounted virtual reality display, augmented reality display, monitor, speaker, haptic device, holographic display, smart wearable device, or a smart handheld device.

In yet another aspect, a non-transitory computer-readable storage medium with instructions stored thereon that, when executed by a processor, cause the processor to perform a method of representing symptoms and symptom alleviation is provided. The method comprises creating, by one or more processors, a first digital model for generating a sensory environment comprising first sensory signals; causing an output device to execute the first digital model to generate the sensory environment; creating a second digital model for a symptom, wherein the second digital model causes generation of second sensory signals; causing the output device to generate the second sensory signals within the sensory environment based on the second digital model; creating a third digital model of an alleviation or removal of the symptom based on the first or the second digital models, wherein the third digital model causes generation of third sensory signals, and wherein at least a portion of the second sensory signals and/or third sensory signals change continuously over time to human perception; and causing the output device to generate the third sensory signals within the sensory environment based on the third digital model.

BRIEF DESCRIPTION OF THE DRAWINGS

The present disclosed technologies are illustrated by way of example, and not by way of limitation, in the figures of the accompanying drawings and in which like reference numerals refer to similar elements and in which:

FIG. 3 describes exemplary operations of the system disclosed herein.

Figure 1:
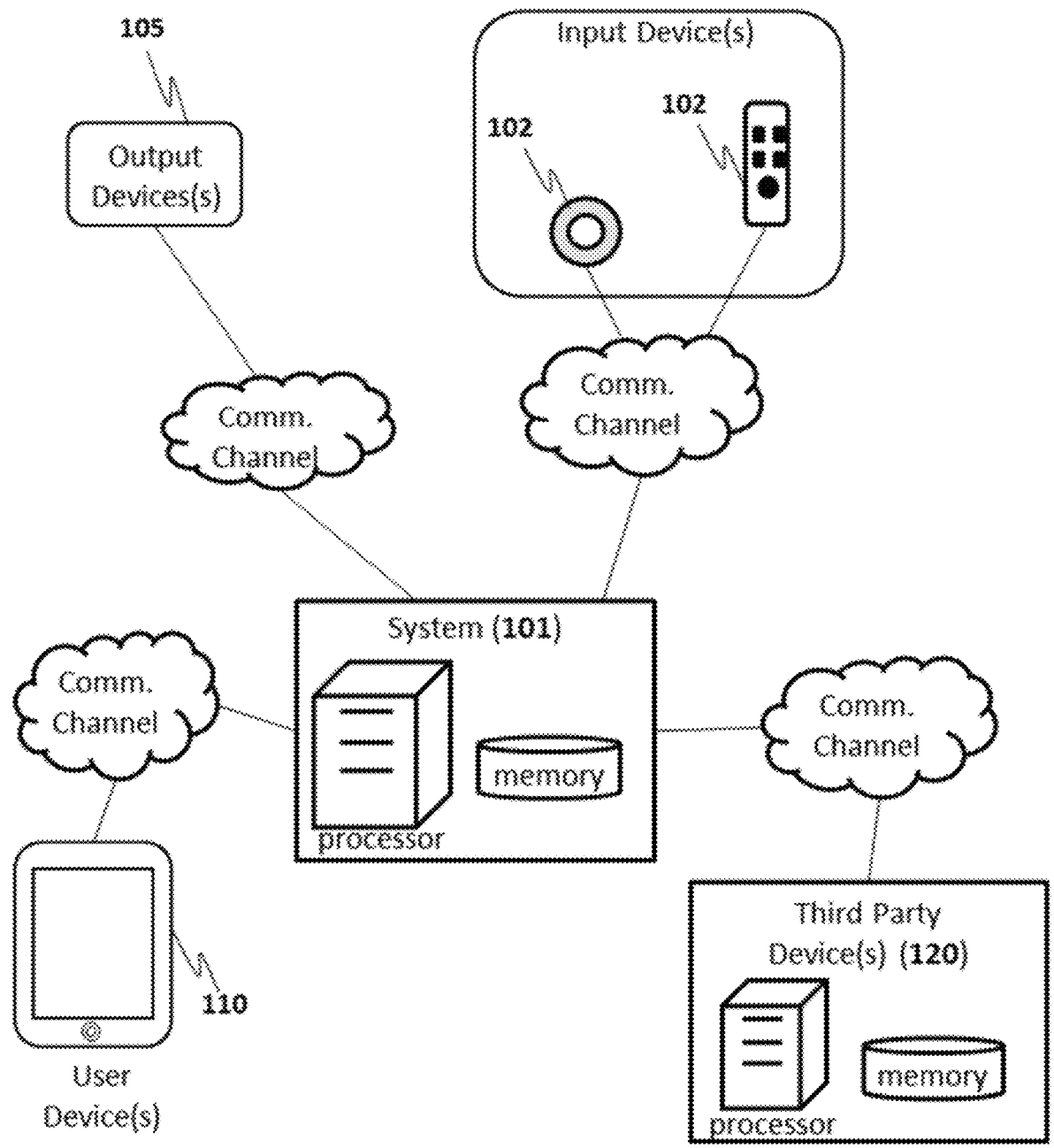
FIG. 1 illustrates an exemplary environment in which the system disclosed in the present application can operate.

The novel features of the disclosed technologies are set forth with particularity in the appended claims. A better understanding of the features and advantages of the present invention will be obtained by reference to the following detailed description that sets forth illustrative embodiments, in which the principles of the invention are utilized.

DETAILED DESCRIPTION

Unless otherwise defined, all technical terms used herein have the same meaning as commonly understood by one of ordinary skill in the art to which this invention belongs. As used in this specification and the appended claims, the singular forms "a," "an," and "the" include plural references unless the context clearly dictates otherwise. Any reference to "or" herein is intended to encompass "and/or" unless otherwise stated.

A "sensory environment" described herein means a computer-generated environment or a computer enhanced environment (e.g. augmented reality) comprising sensory signals representing a context, for representing symptoms and symptom alleviation processes. For example, the sensory environment can include representations of a room or landscape, avatars, virtual control panels, etc. Further details and embodiments of the sensory environment are described below.

"Sensory Signals" (also referred to as a "sensory representation" or a "representation") described herein means any signal which can stimulate or impact the human (or animal) senses, eyes, ears, skin, nose, limbs, body, brain, mind or nervous system. Examples include but are not limited to: audio, visual, tactile, or olfactory signals. They also include signals which can impact the human (or animal) body, brain or nervous system without being consciously perceived; for example, transcranial direct current stimulation. In some preferred embodiments, the sensory signals are created in or in combination with virtual reality, augmented reality, or holography. Further details and embodiments of the sensory signals are described below.

A "symptom" described herein means any psychological or physical health aspect, particularly those related to pain, injury, physical or psychological suffering, illness or disease. Further details and embodiments of the symptom are described below. A "symptom" as used herein can refer to a simple, specific psychological or physical health aspect (e.g., a burning pain sensation localized on the skin), or to a complex set or grouping of psychological or physical health aspects (e.g., long-term chronic back pain in combination with sciatica).

"Out-of-Body Experience" (OBE) described herein means a phenomenon in which a person typically experiences a sensation of the consciousness leaving the body. Often the person experiences a sensation of floating above/beside the body. One way to manifest this experience is to provide the user with a view of an avatar (virtual self) representing the user in a virtual reality environment from a third-person perspective such that the avatar appears to be about two meters in front of the user. Using virtual reality controllers, the user can move the limbs of the avatar. The user is given a series of actions and activities which lead the user to self-identify with the avatar, even though the user sees it from a third-person perspective. In addition to the active influence the user has on the virtual-reality environment, other objects in the virtual-reality environment interact with the avatar and the real self; for example, an object in the virtual environment hits the avatar. At the same time, the user feels a strong pulse in a haptic vest worn by the user in a location corresponding to the place the avatar was hit. This illusion creates a paradox in the user's brain between visual and tactile signals. The user sees the user's virtual self two meters ahead but experiences touch in the real physical location. This can lead to an out-of-body type of experience. Another method for manifesting the out-of-body experience is to start the user in a first person view in the avatar, allowing the user to engage in various activities and interact with the virtual-reality environment, including receiving tactile response. This allows the user's brain to self-identify with the avatar and to geo-locate the position of the avatar. The view of the avatar to the user is then moved from a first-person view out of the body into a third-person view; however, the user maintains control over the movements of the avatar and continues to receive tactile feedback. The user's brain will often continue to self-identify and geo-locate the avatar, leading to a sense of the consciousness having left the body and controlling it from afar (or the body having left the consciousness behind). Further details and embodiments of the OBE are described below.

"Self-Perception" described herein means a mechanism in which the brain (consciousness) identifies with and locates the physical body. Self-perception also includes a mechanism by which the brain identifies and locates different parts of the body (e.g., where is the right arm; where is the right arm in relation to the torso). Self-perception can be fully or partially manipulated in OBE. Examples of how such manipulation can be manifested are explained in the definition of OBE above. Further details and embodiments of the self-perception are described below.

Regardless of whether a visual cue or source of the symptom (e.g., pain) is known, the technologies can be applied. Unlike mirror therapy-based solutions for pain, the present technologies allow users (e.g., patients) or their helpers (e.g., family members, physicians or computing systems) to create digital models of symptom (e.g., pain, malady, wound, bothersome sensations), even if there is no physical manifestation of the symptom, such as a missing or injured limb or some other injury. Furthermore, the disclosed technologies can enable creation of sensor signals to form an immersive environment, such as a virtual reality or an augmented reality environment, that more readily enables the brain to accept the offered stimuli as real and that allows subjects to believe improvements in their symptoms (e.g., relieving pain) or trust their own power to control the improvement.

Figure 2:
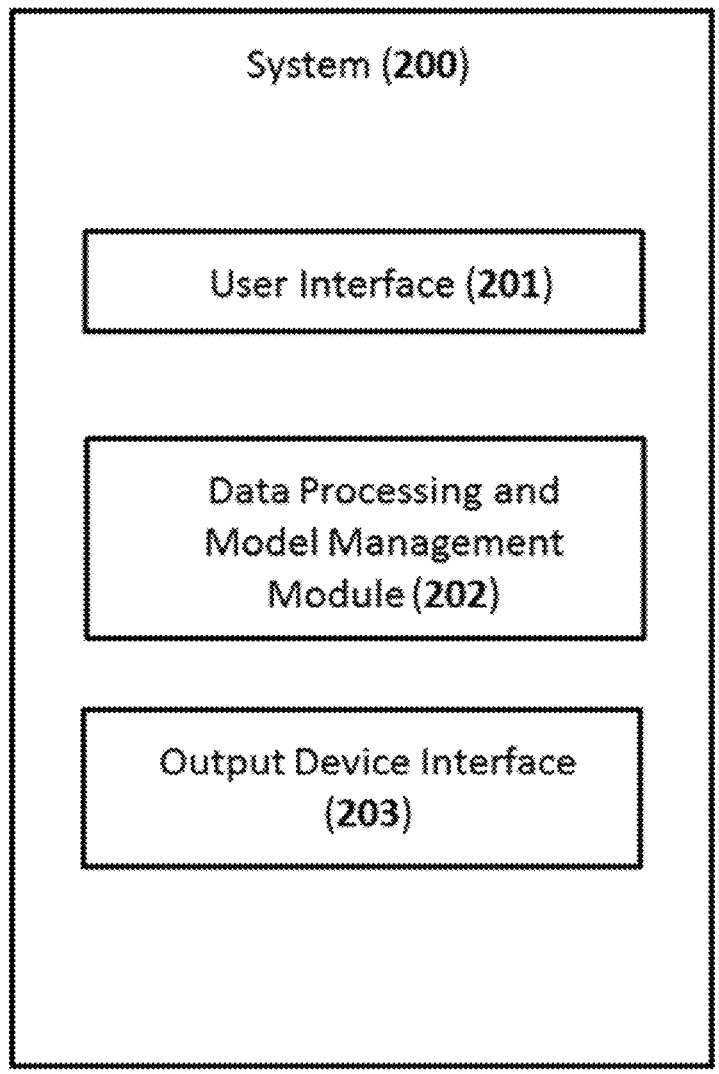
FIG. 2 illustrates an exemplary functional structure of the system.

In various embodiments, the systems, methods, media disclosed herein include a computing system, or use of the same. FIG. 1 illustrates an exemplary computing environment in which the system disclosed in the present application can operate. The system 101 comprises one or more processors and one or more memories. FIG. 2 illustrates exemplary modules of the system. Referring to FIG. 2, a system 200 comprises a user interface 201 receiving inputs from user and generating outputs to the user. The system 200 further comprises a data processing and model management module 202. The module 202 processes input data from the user, a helper (e.g. physician, computer), or other devices, performs analysis and generates digital models for symptoms, symptom alleviation methods, etc. for transmission to output devices that are capable of producing sensory signals. The module 202 uses a series of rules or algorithms to effectively change, move, reduce, remove, or improve representations of symptoms. The system 200 further comprises an output device interface 203 to communicate with output devices, including transmitting the digital models to the output devices.

These modules can be implemented as general or specific-purpose hardware, software, or firmware (or any combination thereof) components. For example, a general computer executes computing instructions of the technologies, or a customized computing device (e.g., FPGA, ASIC, Raspberry, industrial computer, etc.) is implemented to realize the technologies disclosed herein. Modules are typically functional components that can generate useful data or other output using specified input(s). A module may or may not be self-contained. A module can be optional. Depending upon implementation-specific or other considerations, the modules may be centralized or distributed functionally or physically. The interactions among these modules are described in detail below.

In some embodiments, the system 101 can communicate with one or more input devices 102 through a communication channel. The input device 102 generally receives data from a user. The communication channel can be a wired connection or through a wireless connection. Examples of a communication channel include the Internet, a cellular network, or a short-range wireless network. In some cases, the input device 102 is part of the system 101. Examples of input devices include, but not limited to, keyboards, mice, trackball, track pad, joystick, game controller, stylus, sensory environment controllers, remote controller, gaming console, microphones, touchpads, biometric readers, biological signals acquisition apparatus, and sensors. In some embodiments, the input device is a pointing device including, by way of non-limiting examples, a mouse. In some embodiments, the input device is a touch screen or a multi-touch screen. In other embodiments, the input device is a microphone to capture voice or other sound input. In other embodiments, the input device is a video camera or other sensor to capture motion or visual input. In further embodiments, the input device is a Kinect, Leap Motion, or the like. In still further embodiments, the input device is a combination of devices such as those disclosed herein.

A sensor records actions or sensory signals of a user. Examples of sensors include, but not limited to, cameras, microphones, position sensors, RF tags, speed sensors, temperature sensors, liquid sensors, motion sensors, pressure sensors, electric current sensors, electromagnetic sensors, X-ray sensors, light sensors, and electric voltage sensors. The input device 102 can serve as an interaction tool for the user interacting with a sensory environment, symptom representation, or symptom alleviation representation enabled by the system. Inputs acquired by the input device 102 include, but not limited to, images, videos, sounds, voices, speech, motion, and biometric signals. In some embodiments, input signals include symptom descriptions and/or sensory signals of symptoms. In some embodiments, input signals are analyzed by a processor to interpret user actions, user interactions, and user perceptions.

Referring again to FIG. 1, the system can communicate with one or more output devices 105 through a communication channel. The output device 105 generally outputs sensory signals that generally stimulate human (animal) senses, such as audio or video signals. The communication channel can be a wired connection or through a wireless network. In some cases, the output device 105 is part of the system 101. Examples of output devices include, but not limited to, computer displays, head-mounted virtual reality displays, augmented reality displays, projectors, holographic projectors, speakers, two-dimensional (2-D) printers, three-dimensional (3-D) printers, speech-generating devices, televisions, smartphone, video cards, sound cards, plotters, flat panels, laser pointers, vest, haptic device, biological signal stimulators, and digital scent generators. An output device 105 may comprise a display device. In some cases, the output device 105 is integrated into the system 101. Alternatively, the input device 102 and the output device 105 are integrated into a single apparatus separate from the system 101. For instance, a sensory environment controller comprises one or more sensors to allow collections of signals related to the user's actions; on the other hand, the controller comprises a light source to project a digital object in the sensory environment.

Referring again to FIG. 1, the system may communicate with one or more user devices 110 through a communication channel. The user device 110 is typically an integrated device that includes an input device or an output device. The user device 110 generally receives input data from a user or displays output data to a user. The communication channel can be a wired connection or through a wireless network. In some cases, the user device 110 is part of the system 101 or comprises the system 101. Examples of the user device include, but not limited to, desktop computers, smartphones, tablets, and laptops. In some embodiments, the user device 110 is used by a same user of the system 101. In some instances, the user device 110 is used by a second user (such as a family member, or a physician). The user device 110 may be used to transmit additional instructions (e.g., commands on a sensory environment, symptoms or symptom alleviation method) to the system 101, and/or to receive output information (e.g., the sensory environment, digital objects in the sensory environment, and information regarding symptoms of the user of the device 101) from the system 101.

Referring again to FIG. 1, the system optionally communicates with one or more servers or devices 120 from a third party through a communication channel. The communication channel can be a wired connection or through a wireless network. Examples of third parties include, but not limited to, hospitals, government agencies, public information providers, banks, news providers, health care providers, and family members. In some embodiments, the third party device 120 transmits relevant data of the user of the system 101 to the system 101, and the sensory representations created by the system 101 can be adjusted accordingly. In some embodiments, third-party data include, but not limited to, diagnostic data, vital sign data, neuroimaging data, nociceptor activity data, central nervous activity (CNS) data, heart rate, heart rate variability, galvanic skin response, brain waves, EEG data, blood pressure, breathing rate, diaphoresis, pupil dilation, eye movement, temperature, or facial expression data. In some embodiments the third party device 120 receives data from the system 101. In some embodiments this data includes, but is not limited to, frequency of use of the system or changes in symptoms.

FIG. 3 describes exemplary steps or operations performed by the system disclosed herein. In some embodiments, not all of the operations are required. In other embodiments, some of the operations may be performed in a different order. Referring to FIG. 3, in operation 302, the system creates a first digital model that represents a context for representing a symptom and the symptom alleviation process. The first digital model enables generation of a sensory environment comprising first sensory signals. In some embodiments, the sensory environment comprises representations of a user or the surroundings. In some cases, the sensory environment comprises objects representing, for example, a scene, a user's avatar, a control panel, an interface, etc. In operation 304, the system creates a second digital model for a symptom that enables generation of second sensory signals and a third digital model for alleviation of the symptom that enables generation of third sensory signals. The sensory representations may comprise visual, audio, tactile, olfactory, or other (e.g., thermal, gustatory)

sensory signals. At least some of the second sensory signals and third sensory signals change continuously over time to human perception.

In some embodiments, the system can allow a user to customize different aspects of the digital models based on user input to match representations of the symptom or the symptom alleviation with the user's experience or preference. For example, the user can indicate the type, location, size, shape, frequency, intensity, or other attributes of the symptom (e.g., pain, bothersomeness), and the user can indicate the duration, manner, or other aspects of the symptom alleviation. For example, in one embodiment, the system can allow the user to select from a plurality of pain types (e.g., aching, throbbing, sore, stabbing, shooting, stabbing, cramping, gnawing, splitting, heavy or burning) and then modify the pain's location, size, intensity, frequency, depth or saturation. These descriptive symptom features may be modified by adjusting values for each of the features along a spectrum or set of possible values, including adjusting a feature to a zero/mute/null value, a maximum value, or one or more values therebetween. For further example, the system allows the user to choose from one of the following symptom alleviation methods: showing the symptom becoming smaller; reducing in severity or frequency; changing in color or healing; moving the symptom from one part of the body to another; spreading the symptom from one focal point to a more general area; washing the symptom away with a liquid or gas; cooling or warming the affected area of the body; moving the symptom into another body or physical representation (e.g. avatar) separate from the representation of the user (e.g. the user's avatar); creating an augmented experience in which the user experiences leaving his physical body behind; simulating an out-of-body experience, in which the symptom is left behind; improving mobility, motion or function of part or all of the body.

Further, in operation 306, the system causes output devices generate the first, second and third sensory signals (e.g., images, sound, vibration), at least some of which change continuously over time to the user's perception. In some embodiments, the system sends the first, second, or third digital models to the output devices and instructs the output devices to generate the first, second, or third sensory signals. The system can also cause the output devices to generate sensory signals that change continuously over time beyond human perception. The system can send the first, second, or third sensory signals to the same output device or different ones, at the same time or at different times, collectively or individually.

In some embodiments, in operation 308, the system analyzes user response to the sensory signals. The analysis can comprise extracting biometric signal components from a device (e.g., user device 110, input device 102 or third party device 120 in FIG. 1) to understand the behavior or instructions of the user. In addition, when a user performs an action or an interaction, one or more digital models created by operation 302 or 304 may change, and operation 302 or 304 or 306 is executed to modify the first, second, or third digital models, which lead to updated first, second or third sensory signals. In some cases, new digital models or sensory signals are created, and/or existing digital models or sensory signals are deleted.

In some embodiments, part or all of the aspects of the digital models are saved by means of a digital, electronic or another format. There is no limitation that the related data reside on the system. However, computing modules and data may be hosted on another computational device, such as a wired or wireless computer or server, or in the cloud.

Figure 4:
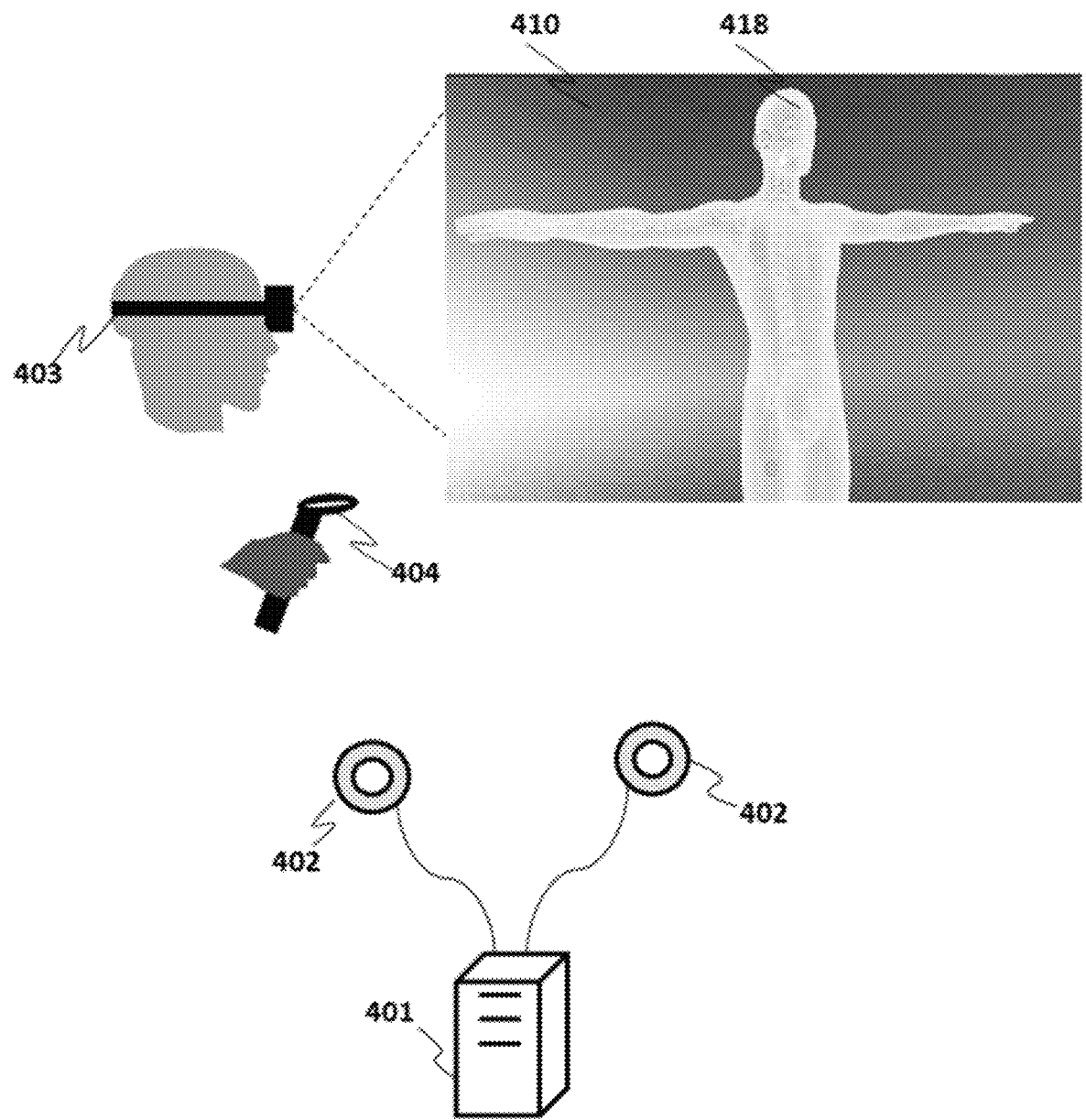
FIG. 4 illustrates an exemplary presentation of or interaction with a sensory environment.

In various embodiments, the systems, methods, media disclosed herein enable creation of sensory signals that form an immersive experience based on virtual reality, augmented reality, holography, etcetera. FIG. 4 illustrates an exemplary presentation of or interaction with a sensory environment. Referring to FIG. 4, a system comprises a digital processing device 401 configured to create a sensory environment 410. The device 401 can be coupled with sensors 402. The sensors 402 track positions and/or movements of the user's body, head, hands, fingers, feet, toes, limbs, elbows, lips, eyes, or eyebrows; in some cases, the sensors 402 record sounds, and voices. The user wears a head-mounted display (HMD) 403 to immerse himself into the sensory environment 410 displayed in the HMD 403. Further, the user can use a physical controller 404 to make interactions with the sensory environment 410.

In some embodiments, the system 401 creates a model of a user 418. The system 401 can also create a virtual control panel in the sensory environment with which a user can interact to provide control commands or input data to the system, such as specification of the user representation, a symptom, or a symptom alleviation method. In addition, the system can allow incorporation of forms of sensory signals, such as audio, into the sensory environment. For example, the system can cause the playing of serene, new-age music in the background. The system subsequently causes generation of sensory signals representing symptoms and symptom alleviation within the sensor environment. Such enhanced sensory environment 410 can be powerful in influencing the user, because it allows the user to be immersed in a vivid experience of symptom alleviation, which can lead the brain to believe that what is being seen, heard, or otherwise sensed is real. Further, the sensory environment can be useful in providing an audio-visual stimulus to guide users towards different perceptions of their pain, physical or psychological capabilities, or symptoms.

In some embodiments, the sensory environment 410 comprises a 2-D or 3-D avatar 418 representing the user. In some embodiments, the system can allow a user to choose from a list of predetermined avatars or to build one from scratch. Furthermore, the system can enable the user to customize various aspects of the user model, such as size, location, movement, etc. For example, the user can enable changes in the digital models according to time changes. The avatar can display exterior appearance of the user, and it may additionally include representations of internal anatomy of the user. In some embodiments, one or more views of the user body are displayed, such as a first person point of view, a perspective view, a front view, a side view, a back view, a top view, or a bottom view, simultaneously in different avatars or at different times as an avatar switches forms. The user is allowed to explore the avatars from different locations, different angles, etc. For example, a user may prefer that the avatar assumes a first-person view so that the user feels like looking inside the user's own body and can more vividly experience the symptom being driven out of the body.

In some embodiments, the user can sense at least one representation 418 of the body in front of the user (corresponding to a mirror image). The representation may represent the user or another person (e.g., a family member, a patient, a physician, etc.) meaningful to the user. The system may also present multiple avatars, including a first one representing the user and a second one representing a significant other, and allows the two avatars to interact. For example, the second avatar can be speaking to the first avatar or taking the pain away from the first avatar for symptom alleviation, as further discussed below. The system may also present multiple avatars representing different versions of the user; for example, one with pain, the other without pain. The system may also present a non-human representation of or a metaphor for the user.

Figure 5A:
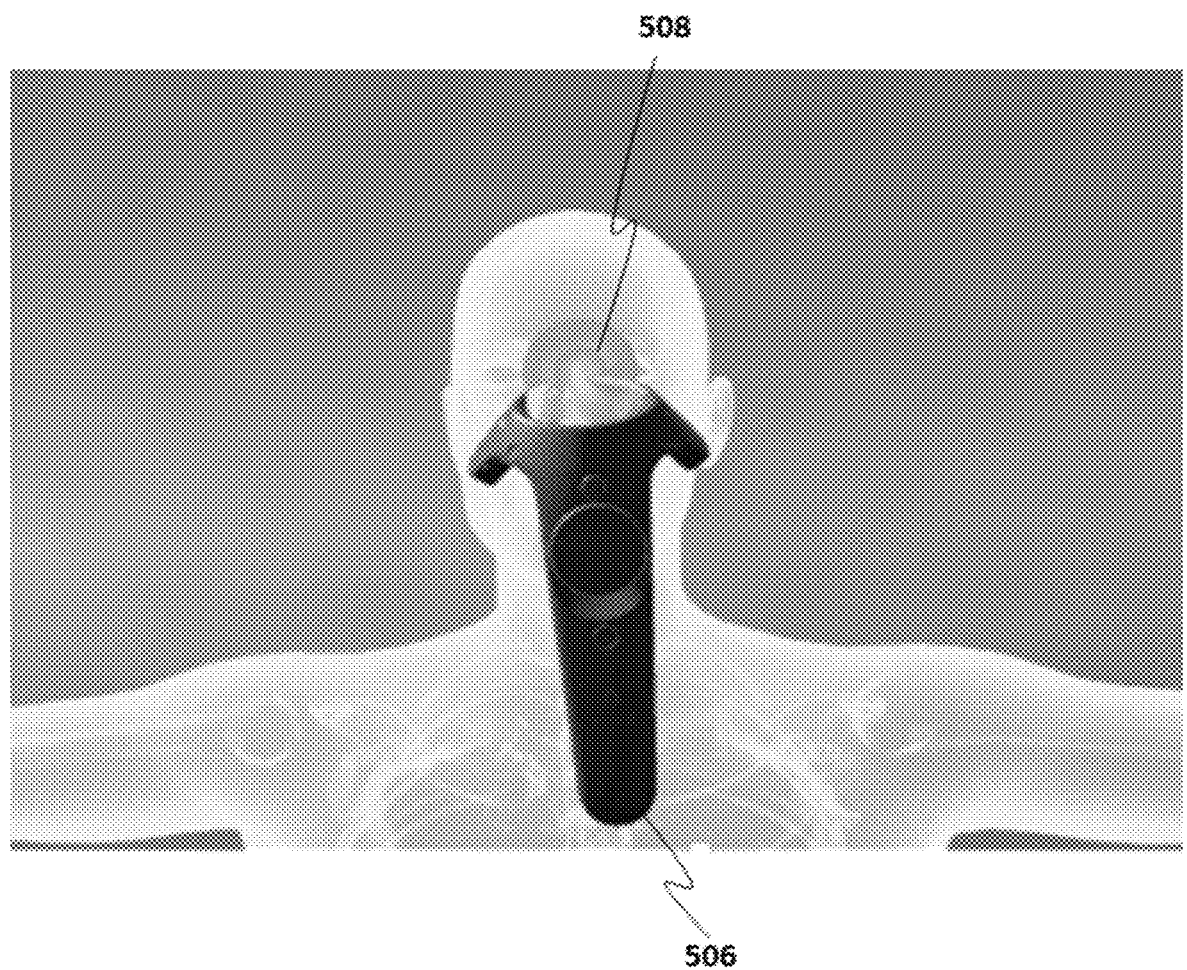
FIG. 5A illustrates an exemplary user operation to provide a symptom description.
Figure 5B:
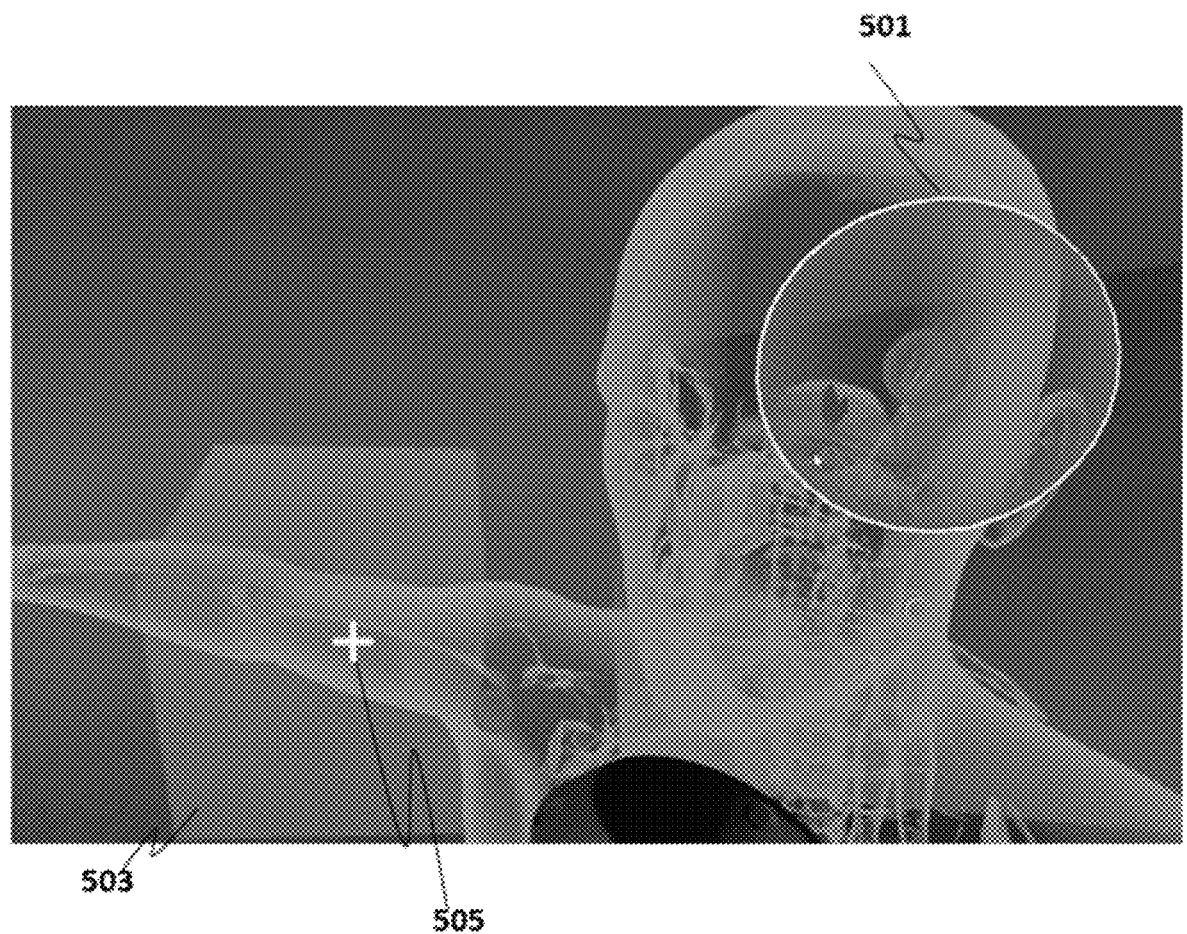
FIG. 5B illustrates an exemplary user operation to provide a further symptom description by managing a digital model of the symptom.

FIG. 5A illustrates an exemplary user operation to provide a symptom description (e.g., a selection of a symptom, a selection from a symptom template, or a more customized description). FIG. 5B illustrates an exemplary user operation to provide a further symptom description by managing a digital model of the symptom. In some embodiments, based on user input, the system creates digital models of symptoms (i.e., symptom digital models)—such as pain, anxiety, fear, or any other physical or psychological manifestations—digital models of a source of the symptoms, or digital models of a metaphor for the symptoms. In some cases, the system can create digital models of the source of or reason for (e.g., injury, wound, or tissue damage of) the symptom (e.g., pain or other health aspect such as bothersomeness/bothersome sensations). The system can also allow a user to choose or specify the nature or form of symptom representation. For example, the nature of a pain can be aching, throbbing, sore, stabbing, shooting, stabbing, cramping, gnawing, splitting, heavy, burning, etc. The system can create a digital model for the symptom that captures such qualities, for example, by incorporating an object normally used to produce such effects. The symptom can otherwise be represented more abstractly as a red dot, a vicious animal, something that arouses an unpleasant feeling in the user, etc. The system can then allow the user to specify the locations of the symptom. For example, the system can initially show a virtual representation 508 of a symptom in the sensory environment and then allow the user using the controller 506 to move that virtual representation to the initial location, such as between the eyes in the head. The user can work with multiple, different representations of the same or different symptoms at once. For example, the same symptom can be represented visually and by audio, and multiple symptoms can be shown visually in different locations of the avatar.

In some embodiments, the system can allow a user to specify or adjust key characteristics of a symptom (e.g., a previously selected or previously described symptom) to more accurately reflect the user's own experience of the symptom. For example, the system can present a virtual cube or coordinate system 503, or some other control console, in the sensory environment to represent the values (coordinates) of three key characteristics of a symptom (e.g., frequency, intensity and saturation), and the user can specify the values (e.g., from 0 to 100 or some other suitable range) of each such characteristic by manipulating a crosshair coordinates tracker 505 in the virtual cube 503. In response to the user input, the system can adjust the digital model for the symptom and thus the virtual representation of the symptom 501 accordingly. Examples of such quantifiable or moldable characteristics include, but not limited to a size, duration, frequency, intensity, topography, shape, etc. For example, the sensory environment can include a display of a darker region to indicate a higher intensity of the symptom and a pulsing effect to indicate frequency.

In some embodiments, a digital model of a symptom (e.g., pain) may be created based on one or more templates; alternatively, it can be created new by the user (e.g., drawn "free-hand" by the user). The system can prompt or allow a user to provide information regarding the symptom. The user can provide textual descriptions, photos, graphical illustrations, sound bites, etc. that characterize the symptom. The user can further indicate a source of the symptom, a level of the symptom, and a history of the symptom. Alternatively, the user can answer a series of questions or just choose from one of the predetermined templates. Such predetermined templates can be simple (e.g., a throbbing sphere representing throbbing pain), or can represent a complex set of symptoms. Such predetermined templates may be developed by generalizing or averaging symptom indications provided by others or may represent a predetermined set of commonly described symptoms. Examples of such predetermined templates might include sets of symptom representations most common to people with chronic lower back and sciatic pain, a rotator cuff injury, a pinched nerve in the shoulder or neck, a knee injury, or a migraine. The digital models can be dynamic; for example, a representation of a throbbing pain would actually throb continuously in the sensory environment. Furthermore, the digital models can be customized to match the user's own experience of the symptom; for example, match the frequency and intensity of throbbing pain in the user's own body. In some embodiments, the digital models of symptoms are created or edited by a user or a computer system (e.g. artificial intelligence or machine learning device or a care-giving robot). Furthermore, the digital models can be created based on incorporating/uploading an independent file, such as sounds, voices, descriptions, medical history, photos, images, and videos.

Figure 6:
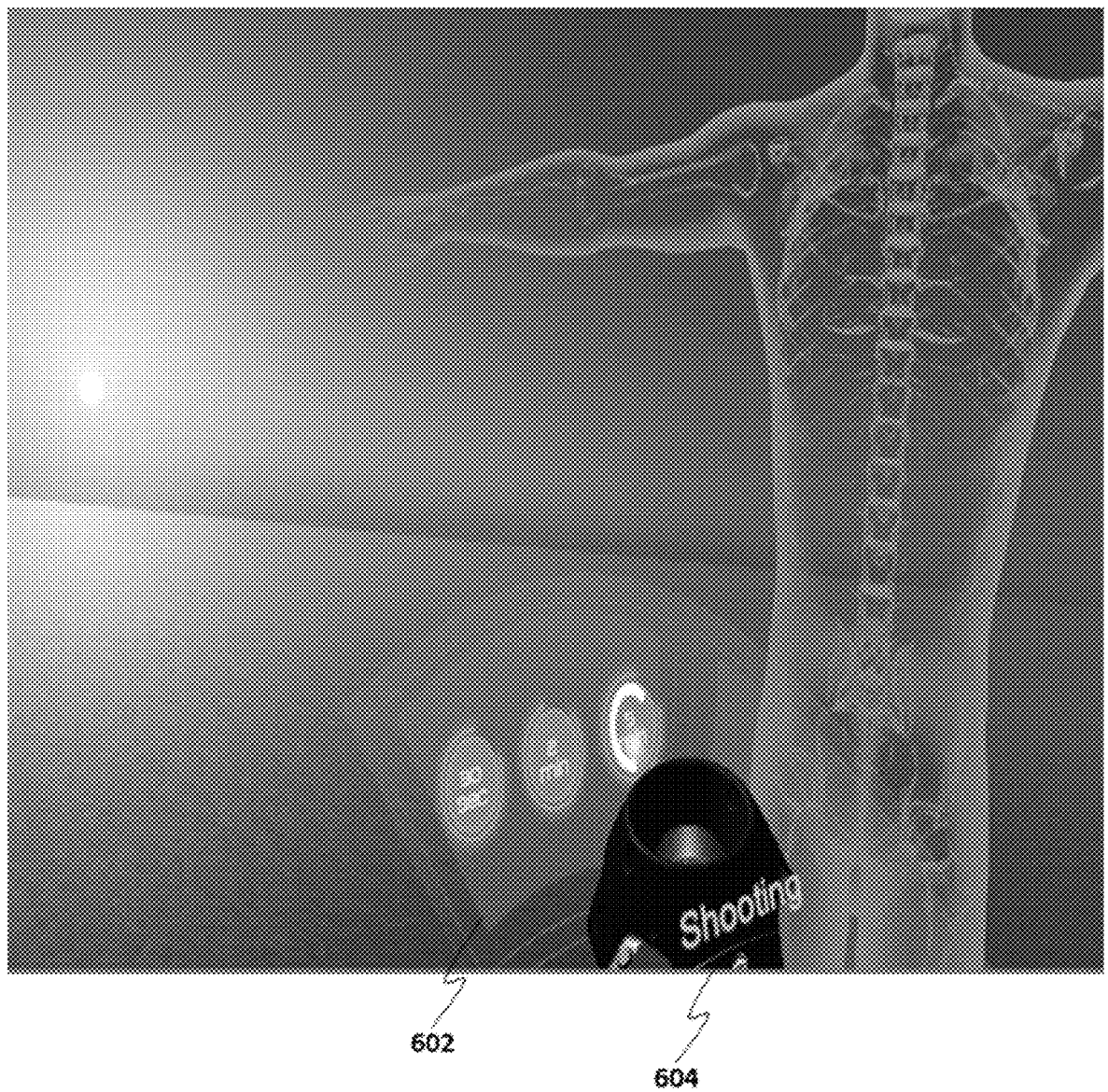
FIG. 6 illustrates an exemplary user operation to edit or adjust features of symptom alleviation.

FIG. 6 illustrates an exemplary user operation to edit or adjust features of symptom alleviation. In some cases, based on user input, the system creates a digital model that represents a treatment or alleviation method. The user is allowed to specify varying parameters such as duration, intensity, frequency, manner, or quality associated with the method. In FIG. 6, the system causes the display of a virtual panel 602 in the sensory environment, which allows a user to indicate using the controller 604 the time it takes for the symptom to disappear, to move to a different location, to assume a substantially different form, or the time it takes before taking a break, before someone else intervenes in the process, etc. The same or different user interfaces that allow the user to describe the symptom can be used to allow the user to describe the symptom alleviation process.

In some embodiments, the system can provide the user with a list of symptom alleviation, reduction, or elimination representations to choose from. Example methods include a reduction in size of; an increase of a distance from; an evaporation of; a recoloring/discoloring of; a dilution of; a diffusion of; a dissipation of; a relocation of (to another portion of the user's body, or another location outside the user's body, including another location within another body); a reduction in frequency of; a distortion of; a disappearing of; a washing or blowing away of; a silencing of; a slowing of; a melting of; a healing of; a stilling; or a cooling of the virtual representation of the symptom. The system can allow the user to control specific aspects of each method. For example, for reduction, the user can be allowed to change the rate of reduction; for discoloration, the user can be allowed to specify the changing colors. The user can also be allowed to manage multiple symptom alleviation representations at the same time or different times. As one example, the user can request that the system show water poured over the symptom representation and if that does not suffice further show fire burning over the pain representation after a specific period of time. As another example, the system can show a second avatar hugging the user's avatar or massaging the shoulder of the user's avatar or singing a song to the user's avatar, all while the user's avatar is rubbing the symptom representation. In some cases, these symptom alleviation representations enable the user to have an out-of-body experience, where the user's perception of his body self-perception is manipulated such that the user perceives a separation from the physical boundaries of the body.

Figure 7:
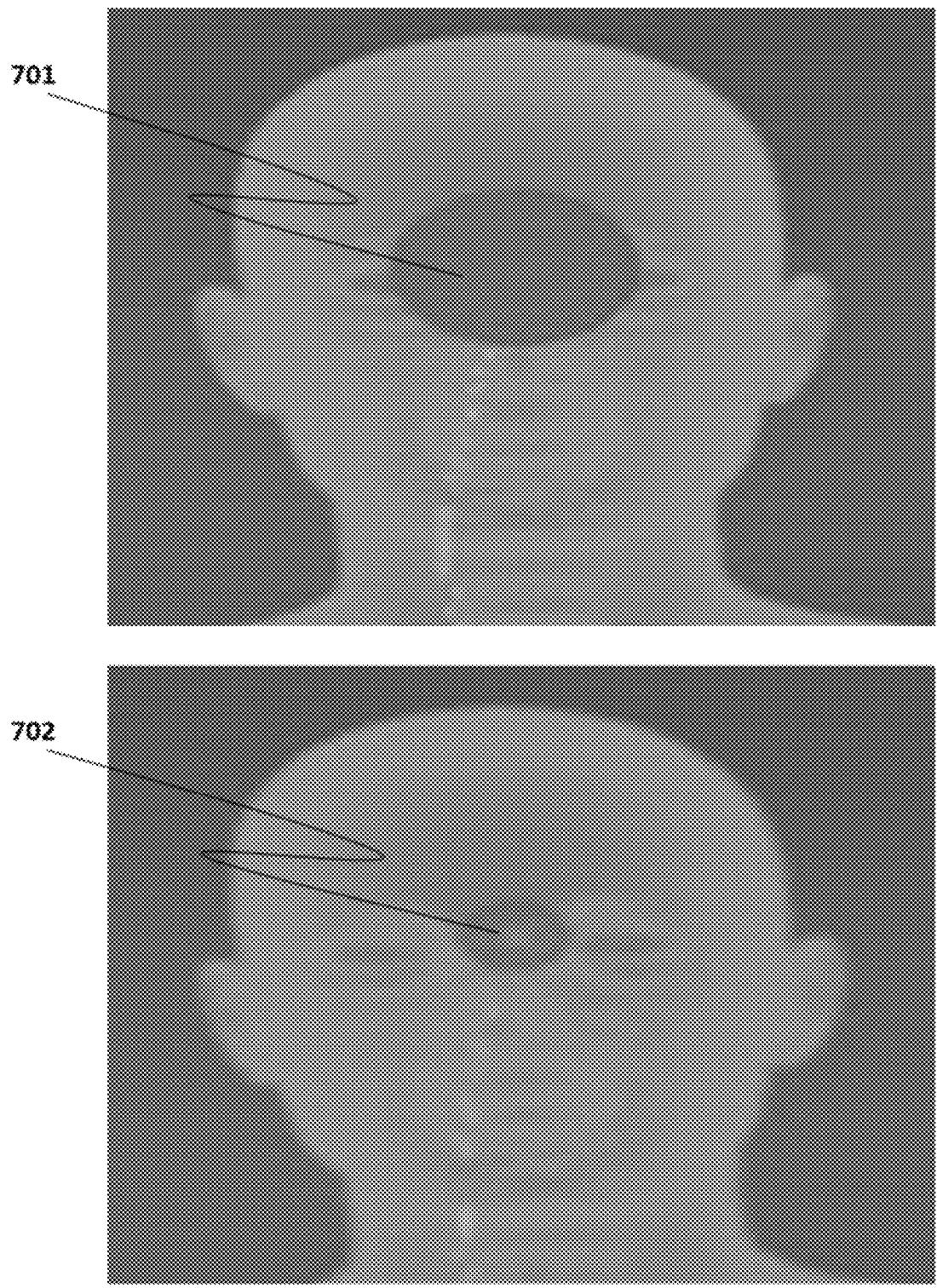
FIG. 7 illustrates an exemplary digital model of symptom improvement, in a passive mode.

In some embodiments, the representation of symptom alleviation can be made in a passive, active, or responsive mode, and a user is allowed to select one or more of these modes. An example of a passive mode can be a case where the user is simply observing a change in symptom development (e.g., watching and meditating on the symptom representation that gets smaller and slower until it disappears). FIG. 7 illustrates an exemplary representation of symptom improvement, in a passive mode. The user can select a treatment of a symptom, resulting in the presentation of an improvement, such as a decline, removal, or healing of the symptom or the cause of the symptom (e.g., wound). Referring to FIG. 7, a symptom representation 701 is shown as a large sphere before any alleviation is applied; after the alleviation takes effect, the symptom representation 702 shrinks. The system automatically and continuously adjusts the symptom representation towards a smaller size based on a symptom alleviation specification provided by the user earlier without requiring further user input.

Figure 8:
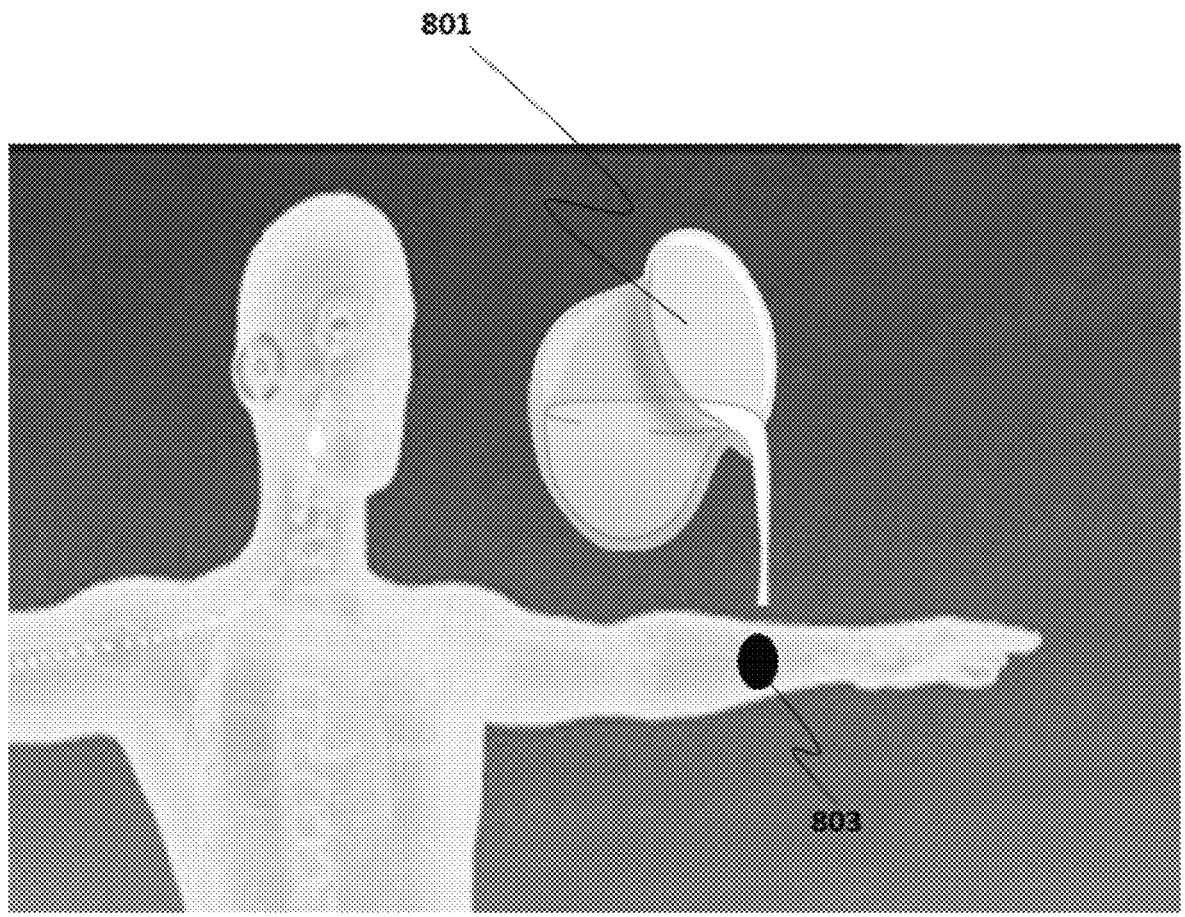
FIG. 8 illustrates an exemplary digital model of symptom alleviation, in an active mode.

In an active mode, the user interacts with or "causes" the healing effect. FIG. 8 illustrates an exemplary representation of symptom alleviation, in an active mode. The user uses a controller in the real world to actively control the action of pouring water over the symptom representation. The user causes the avatar to pour healing water 801 over the symptom representation 803, which is then shown to be washed away. The system can also show the effect after pouring the healing water. The purpose of the active mode would be to reinforce the user's sense of power over the symptom. Over time this sense of empowerment may help change the user's perception of the symptom and/or his relationship with the symptom.

Some embodiments include the use of body movement, range of motion or physical capability or skill. In such embodiments, the user may be asked to make certain movements in the real world, which are represented or mimicked by an avatar in the virtual world. The motion of the avatar may be more than, less than or the same as the real-world motion of the user. One example of the use of such techniques is to convince the user that his or her range of motion is improving or is better than previously perceived. Such information often helps lead to a sense of empowerment over the symptom (e.g., pain and/or bothersomeness/bothersome sensations), a reduction in the anxiety or fear about the symptom and, in some cases, even a reduction in the perception of the symptom.

For example, the digital model may be configured to provide sensory signals (e.g., visual, audio, tactile, olfactory, gustatory, or thermal signals) that function to enable "progressive movement" therapy to the user. This may include adjusting the sensory representation of the symptom in a manner that "nudges" the user into particular movements or a range of motion that the user may have perceived as more painful, or that the user may not have perceived as possible absent the indication from the virtual immersive environment. The symptom may also be represented in a manner that changes with user movement. As an example, the symptom representation may become more intense and/or frequent as a user moves. Over time, as the user repeats the movement, the digital model adjusts the representation of the symptom such that the intensity and/or frequency of the representation is lessened compared to prior movements. For example, the digital model may lessen the intensity/frequency of the representation for the same range of motion and/or slow the rate at which the intensity/frequency rises during the movement, or the system may not trigger any change in the intensity/frequency until much farther into the movement. In this manner, the user's perception of the pain, bothersome sensation, or other symptom is adjusted, and the user can be aided in improving range of motion, lessening anxiety or fear associated with the movement, reducing pain associated with the movement, and/or reducing the perceived experience of the symptom.

In the responsive mode, the system can use biofeedback, which involves capturing one or more aspects of the user's own biometric data. The purpose of using biofeedback is to allow the user to use the internal body functions to regulate the virtual representation of symptom alleviation. Such biofeedback can be used to show the user that the user's physical condition concerning the pain or even other aspects is improving, and to adjust the pain reduction process. In some embodiments, this technique with the biofeedback signal is not actually driving the healing imagery; for example, a sensory representation of shoulder muscle tension driving neck pain may show a reduction in shoulder tension driving a reduction in neck pain; however, the image of declining muscle tension and pain might not be directly tied to the decline in actual shoulder tension as measured by the biofeedback device. In other words, the system could vary from traditional biofeedback techniques.

Examples of biofeedback include, but not limited to, heart rate, heart rate variability, galvanic skin response, brain waves/EEG data, fMRI data, blood pressure, breathing rate, diaphoresis, pupil dilation, eye blinking, eye movement (e.g., saccadic/micro-saccadic movement), temperature, body movement, facial expression data or other data. Biofeedback may also come from a dolorimeter or similar devices to measure pain or calculate a correlation with pain. The biofeedback data may be augmented with other data derived from the hardware and software instantiating the virtual environment (e.g., a virtual reality head mounted display). There are many advantages by integrating biofeedback information. Biofeedback can be used to regulate body functions, which have direct or indirect bearing on the experience of pain; for example, certain types of chronic neck pain increase with tension in the shoulders. If biofeedback can be used to train the user to relax, the user may actually experience less pain in the real body, as well as seeing a reduction in pain in the virtual body (the avatar in the virtual environment).

In some embodiments, the system allows the user to control various aspects of the utilizing biofeedback. For example, the user can specify where to collect biofeedback, how often and for how long biofeedback is to be collected, what types of biofeedback is to be collected, how the biofeedback is to be used or presented, etc. In some embodiments, the system can infer a user's health condition and/or asks the user to provide direct feedback on a level of pain, discomfort, or psychological state. The feedback can be solicited before, during and after the user's experience of symptom alleviation provided by the system. In some embodiments, a user can provide feedback upon the system request, or whenever the user wishes. In some embodiments, the feedback is not supplied by the user, but is automatically collected before, during or after symptom alleviation by examination of all or part of the user's body. Furthermore, as discussed above, the system can enable a user to visualize or otherwise sense the collected biofeedback directly and/or use it to adjust the symptom or the symptom alleviation process.

An example of the use of heart rate biofeedback is as follows. Along with the representation of the user's pain, the system provides a representation of the user's heart rate. As the user feels pain, his or her heart rate tends to rise. Lowering heart rate may help the person relax and in some cases this leads to a reduction in pain. When the user manages to lower the heart rate into a target range, the representation of the pain starts to improve—e.g., decline, dissipate, or "heal." In other words, the system can incorporate biofeedback techniques to provide the user with a way to drive the healing and obtain physical evidence of body condition improvement, while at the same time giving the user physiological training which can help the user reduce sensory pain.

Figure 9:
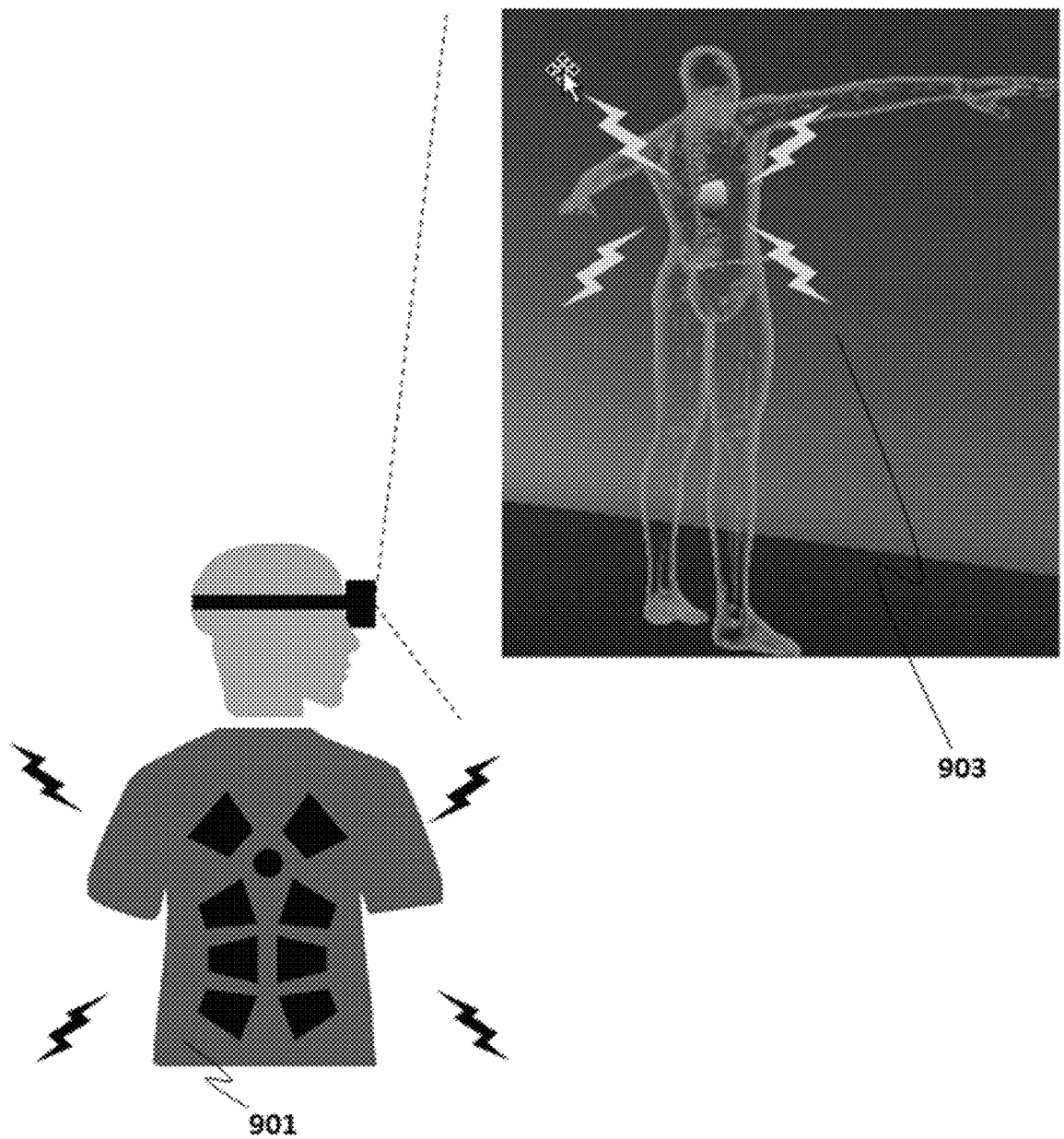
FIG. 9 illustrates an exemplary digital model of a symptom with different types of sensory signals.

FIG. 9 illustrates an exemplary representation of a symptom with different types of sensory signals. In this case, the symptom is a throbbing pain. The haptic vest 901 is configured to vibrate at the same frequency as the throbbing. On the other hand, the system allows the user to further draw a throbbing back pain and choose a healing methodology in which the symptom representation gets smaller and dissipates. The system further causes display of visual signals, such as dynamic images of lightning bolts 903, to represent the throbbing nature and indicate healing in progress through the decreasing intensity of the lightning bolts. As a result, the vibration in the tactile vest 901 which corresponds to the throbbing pain also gets softer and slower. In this manner, the system allows the user to simultaneously experience two types of sensory stimulation through both visual and haptic representations of the throbbing, which may increase the therapeutic effect.

In some embodiments, the creation of the digital model of the symptom or symptom alleviation can be accompanied by audio-visual or other multimedia guidance, such as a guided protocol or instructions, guided meditation, or affirmations. In some embodiments, the audio-visual guidance is used to reinforce a user's sense of empowerment to control the user's symptom. In some embodiments, the multimedia guidance is used to train or reinforce symptom handling techniques, such as cognitive behavioral therapy or specific instructions from a helper (e.g., physician, psychologist). The audio-visual guidance may comprise recordings of the user's own thoughts (e.g., self-affirmations of the patient's ability to control the pain), for example.

Complementary Devices

In various embodiments, the system may comprise other equipment or devices, or use of the same. The other devices, including user devices, sensors, input devices, output devices, or integrated electronic devices, can be coupled with the system to augment the experience of symptoms or symptom alleviation.

In some embodiments, the system comprises or communicates with equipment to provide the user with audio-visual entrainment (AVE) signals or binaural beats. It is possible to modify the brain waves within a human (or animal) with the use of visual or audio signals at specific frequencies. Binaural beats is one example of AVE. A binaural beat is an auditory illusion of a third tone perceived when two different pure-tone sine waves, both with frequencies under 1500 Hz where the difference in frequency is less than a 40 Hz, are provided to a listener, one through each ear. Binaural beats can be used to synchronize brain waves to externally induced signals. Applications may be varied and include inducing a more relaxed state, modulating heart rate variability, etc. The use of AVE may make humans more open to suggestion. In some embodiments, AVE is a useful tool to augment the effect of the technologies—e.g., relaxing the patient to help reduce the experience of pain.

In some embodiments, the system comprises or communicates with equipment to provide tactile or haptic experience in the user, such as a vibration, throbbing, poking. Such a device can be used to augment the power of the illusion of the virtual symptom (e.g., pain) in the virtual environment. For example, a haptic vest in FIG. 9 could vibrate at the same frequency as a throbbing pain drawn in the avatar. During the "healing" process that haptic input could become softer or less intense to match the visual and audio representation of a throbbing pain going away. Tactile/haptic devices are also powerful tools in inducing an out-of-body experience.

In some embodiments, the system comprises or communicates with a heating/cooling device (e.g., radiative heating device, fan, mister, air conditioning device, cold/heat pack applicator, or other device capable of modulating perceived temperature). Similar to haptic devices, the heating/cooling devices are used to enhance the sensation of healing effects. For example, a cooling device can augment a healing method where a burning pain is cooled down. In another example, the heating/cooling device can be used to correspond to the symptom itself (e.g., the temperature of a heat pack corresponds to the user's sensations of a burning pain). In such embodiments, the heating/cooling device can then be adjusted to represent an improvement in the symptom (e.g., a reduction in the temperature of the heat pack representing an easing in the burning pain).

In some embodiments, the system comprises or communicates with a muscle stimulator, a nerve stimulator, a transcutaneous electrical nerve stimulator (TENS), and/or a muscle relaxer. These devices may be external or implanted devices incorporated into some embodiments disclosed herein. Some such devices can be used to help stimulate or relax specific areas of the body to mimic/augment either the symptom (e.g., pain) or healing of the symptom. Some devices can also be used to induce a physical effect in a nerve or muscle that helps create a physical reduction in the symptom (e.g., pain) while the invention helps to drive the psychological factor in the perception of (reduced) pain. For example, certain muscle and nerve stimulators induce a temporary quieting of peripheral nerves, which can create a physical reduction in sensory pain signals to the brain at a time when the invention creates a psychological perception of pain healing effect.

In some embodiments, the system comprises or communicates with a brain or nervous system stimulating device. The brain stimulating device, such as a transcranial direct current stimulation (TDCS) device, a transcranial magnetic stimulations (TMS) device or a spinal cord stimulator, can be added to various embodiments. The application of such an addition varies. One use of TDCS and TMS is to send magnetic waves into the brain, which have shown the ability to reduce sensations of pain. Another use of such a device may be to increase neuroplasticity of the brain.

In some embodiments, the system comprises or communicates with an olfactory device. The olfactory device (e.g., fragrances or smells) can be used to create mood or mental state in a user, thus augmenting the experience. In addition, smell can be a powerful trigger for memories, and thus can become an important anchor or trigger of the healing sensation. For example, a symptom relieving action is performed by the user by interacting with a representation of a symptom, and the system triggers an olfactory device to emit nice smells to relax the user's mood.

In some embodiments, the system comprises or communicates with other integrated computing devices, which include combines one or more of the types of devices discussed above.

Complementary Therapies

In some embodiments, the system is used in combination with prescription and/or non-prescription pharmacological therapies involving the use of various chemical compounds (e.g., drugs pharmaceuticals, vitamins, minerals, etc.). A compound might include agents, which have an analgesic effect, inhibit pain signals, induce relaxation, reduce anxiety, or create a mental state that is more beneficial for neuroplasticity or rewiring.

Digital Processing Devices

In some embodiments, the system described herein includes a digital processing device, or use of the same. In further embodiments, the digital processing device includes one or more hardware central processing units (CPUs) or general purpose graphics processing units (GPGPUs) that carry out the device's functions. The digital processing device may include substantial computational and storage capability, such as a database, an array of rules or algorithms or artificial intelligence (AI), to control the audio-visual or similar content. The digital processing device can perform part or all of the data processing and analysis typically performed by the system. In some embodiments, the digital processing device is optionally connected to a computer network. In other embodiments, the digital processing device is optionally connected to a data storage device.

In accordance with the description herein, suitable digital processing devices include, by way of non-limiting examples, desktop computers, laptop computers, notebook computers, sub-notebook computers, netbook computers, net pad computers, set-top computers, and media streaming devices, handheld computers, Internet appliances, mobile smartphones, tablet computers, personal digital assistants, video game consoles, and vehicles. The digital processing device can also be implemented as a sever farm, a parallel computing device, a cloud-computing platform, etc. Those of skill in the art will recognize that many smartphones are suitable for use in the system described herein. Those of skill in the art will also recognize that select televisions, video players, and digital music players with optional computer network connectivity are suitable for use in the system described herein. Suitable tablet computers include those with booklet, slate, and convertible configurations, known to those of skill in the art.

In some embodiments, the device includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes drives, optical disk drives, and cloud computing based storage. In further embodiments, the storage and/or memory device is a combination of devices such as those disclosed herein.

In some embodiments, the digital processing device includes a display to send visual information to a user. In some embodiments, the display is a cathode ray tube (CRT). In some embodiments, the display is a liquid crystal display (LCD). In further embodiments, the display is a thin film transistor liquid crystal display (TFT-LCD). In some embodiments, the display is an organic light emitting diode (OLED) display. In various further embodiments, on OLED display is a passive-matrix OLED (PMOLED) or active-matrix OLED (AMOLED) display. In some embodiments, the display is a plasma display. In other embodiments, the display is a video projector. In still further embodiments, the display is a combination of devices such as those disclosed herein.

Figure 10:
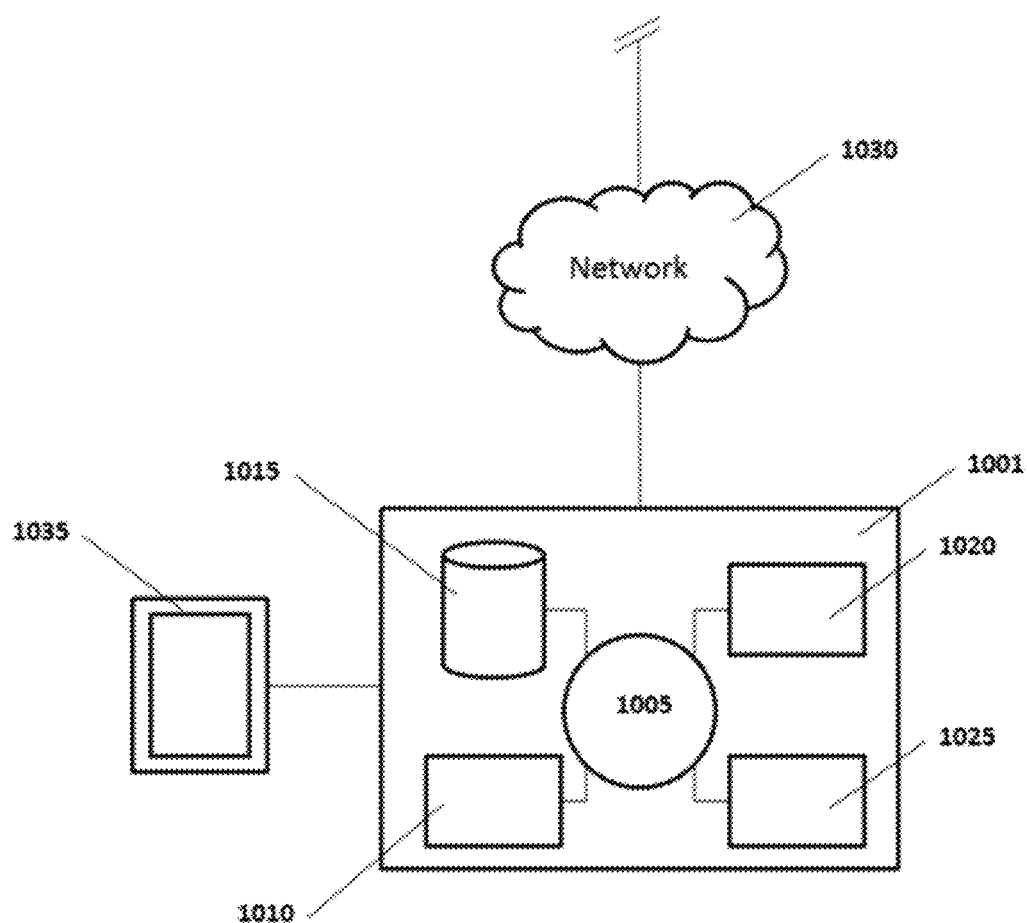
FIG. 10 illustrates an exemplary computing architecture applicable to any computing device discussed herein.

FIG. 10 illustrates an exemplary computing architecture applicable to any computing device discussed herein. In some embodiments, the digital processing device 1001 includes a central processing unit (CPU, also "processor" and "computer processor" herein) 1005, which can be a single core or multi core processor, or a plurality of processors for parallel processing. The digital processing device 1001 also includes memory or memory location 1010 (e.g., random-access memory, read-only memory, flash memory), electronic storage unit 1015 (e.g., hard disk), communication interface 1020 (e.g., network adapter) for communicating with one or more other systems, and peripheral devices 1025, such as cache, other memory, data storage and/or electronic display adapters. The memory 1010, storage unit 1015, interface 1020 and peripheral devices 1025 are in communication with the CPU 1005 through a communication bus (solid lines), such as a motherboard. The outputs can be shown on a display 1035. The storage unit 1015 can be a data storage unit (or data repository) for storing data. The digital processing device 1001 can be operatively coupled to a computer network ("network") 1030 with the aid of the communication interface 1020. The network 1030 can be the Internet, an internet and/or extranet, or an intranet and/or extranet that is in communication with the Internet. The network 1030 in some cases is a telecommunication and/or data network. The network 1030 can include one or more computer servers, which can enable distributed computing, such as cloud computing. The network 1030, in some cases with the aid of the device 1001, can implement a peer-to-peer network, which may enable devices coupled to the device 1001 to behave as a client or a server.

Continuing to refer to FIG. 10, the CPU 1005 can execute a sequence of machine-readable instructions, which can be embodied in a program or software. The instructions may be stored in a memory location, such as the memory 1010. The instructions can be directed to the CPU 1005, which can subsequently program or otherwise configure the CPU 1005 to implement methods of the present disclosure. Examples of operations performed by the CPU 1005 can include fetch, decode, execute, and write back. The CPU 1005 can be part of a circuit, such as an integrated circuit. One or more other components of the device 1001 can be included in the circuit. In some cases, the circuit is an application specific integrated circuit (ASIC) or a field programmable gate array (FPGA).

Continuing to refer to FIG. 10, the storage unit 1015 can store files, such as drivers, libraries and saved programs. The storage unit 1015 can store user data, e.g., user preferences and user programs. The digital processing device 1001 in some cases can include one or more additional data storage units that are external, such as located on a remote server that is in communication through an intranet or the Internet.

Continuing to refer to FIG. 10, the digital processing device 1001 can communicate with one or more remote computer systems through the network 1030. For instance, the device 1001 can communicate with a remote computer system of a user. Examples of remote computer systems include personal computers (e.g., portable PC), slate or tablet PCs (e.g., Apple® iPad, Samsung® Galaxy Tab), telephones, Smart phones (e.g., Apple® iPhone, Android-enabled device, Blackberry®), or personal digital assistants.

Methods as described herein can be implemented by way of machine (e.g., computer processor) executable code stored on an electronic storage location of the digital processing device 1001, such as, for example, on the memory 1010 or electronic storage unit 1015. The machine executable or machine readable code can be provided in the form of software. During use, the code can be executed by the processor 1005. In some cases, the code can be retrieved from the storage unit 1015 and stored on the memory 1010 for ready access by the processor 1005. In some situations, the electronic storage unit 1015 can be precluded, and machine-executable instructions are stored on memory 1010.

Computer Program

In various embodiments, the systems, methods, media disclosed herein include a computer program, or use of the same. The computer program product is embodied in a non-transitory computer-readable medium, the computer program product comprising instructions adapted to effectuate the method above. The technologies can be in the form of a video game, software application, app or software code (or similar electronic means) that can be implemented on a virtual reality, augmented reality, holographic or other electronic device (e.g., tablet or smartphone).

In some embodiments, the platforms, systems, media, and methods disclosed herein include at least one computer program, or use of the same. A computer program includes a sequence of instructions, executable in the digital processing device's CPU, written to perform a specified task. Computer readable instructions may be implemented as program modules, such as functions, objects, Application Programming Interfaces (APIs), data structures, and the like, that perform particular tasks or implement particular abstract data types. In light of the disclosure provided herein, those of skill in the art will recognize that a computer program may be written in various versions of various languages, and may incorporate or make use of pre-existing software programming or game development software.

The functionality of the computer readable instructions may be combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

Non-Transitory Computer Readable Storage Medium

In some embodiments, the platforms, systems, media, and methods disclosed herein include one or more non-transitory computer readable storage media encoded with a program including instructions executable by the operating system of an optionally networked digital processing device. In further embodiments, a computer readable storage medium is a tangible component of a digital processing device. In still further embodiments, a computer readable storage medium is optionally removable from a digital processing device. In some embodiments, a computer readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

Software Modules

In some embodiments, the platforms, systems, media, and methods disclosed herein include software, server, and/or database modules, or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

Databases

In some embodiments, the platforms, systems, media, and methods disclosed herein include one or more databases, or use of the same. In view of the disclosure provided herein, those of skill in the art will recognize that many databases are suitable for storage and retrieval of recorded information (e.g. pain or symptom information). In various embodiments, suitable databases include, by way of non-limiting examples, relational databases, non-relational databases, object oriented databases, object databases, entity-relationship model databases, associative databases, and XML databases. In some embodiments, a database is internet-based. In further embodiments, a database is web-based. In still further embodiments, a database is cloud computing-based. In other embodiments, a database is based on one or more local computer storage devices.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Preferred embodiments include a method of representing symptoms and symptoms alleviation, comprising: creating, by one or more processors, a first digital model for generating a sensory environment comprising first sensory signals; causing an output device to execute the first digital model to generate the sensory environment; creating a second digital model for a symptom, wherein the second digital model causes generation of second sensory signals; causing the output device to generate the second sensory signals within the sensory environment based on the second digital model; creating a third digital model of an alleviation or removal of the symptom based on the first or the second digital models, wherein the third digital model causes generation of third sensory signals, and wherein at least a portion of the second sensory signals and/or third sensory signals change continuously over time to human perception; and causing the output device to generate the third sensory signals within the sensory environment based on the third digital model.

Numbered Paragraphs Corresponding to Inventive Concepts:

In combination with any aforementioned methods in this disclosure, the first, second, or third digital model is a two-dimensional or three-dimensional model.

In combination with any aforementioned methods in this disclosure, the output device comprises multiple devices and the first sensory signals, second sensory signals, and third sensory signals are individually or collectively sent to one or more of the multiple devices.

In combination with any aforementioned methods in this disclosure, the first sensory signals, second sensory signals, or third sensory signals form holographic, virtual-reality, or augmented-reality representations.

In combination with any aforementioned methods in this disclosure, the first, second, or third output device produces audio, visual, tactile or olfactory signals.

In combination with any aforementioned methods in this disclosure, the first sensory signals, second sensory signals, or third sensory signals are produced responsive to user input.

In combination with any aforementioned methods in this disclosure, the method further comprises receiving a description of the symptom, wherein creating the second digital model is based on the description.

In combination with any aforementioned methods in this disclosure, the description of the symptom comprises an illustration of the symptom.

In combination with any aforementioned methods in this disclosure, the description of the symptom comprises one or more of a photo, a video, an animation, a sound, a vibration, or a scent.

In combination with any aforementioned methods in this disclosure, the illustration includes a representation of a wound or tissue damage that caused the symptom.

In combination with any aforementioned methods in this disclosure, the description of the symptom comprises scores for one or more a predefined set of symptom characteristics.

In combination with any aforementioned methods in this disclosure, the description is for various pain types, including one or more of aching, throbbing, sore, stabbing, shooting, stabbing, cramping, gnawing, splitting, heavy, or burning.

In combination with any aforementioned methods in this disclosure, creating the second digital model comprises: acquiring one of a plurality of template models for the symptom; and personalizing the template model based on the description.

In combination with any aforementioned methods in this disclosure, the one template model corresponds to a physical quality of the symptom.

In combination with any aforementioned methods in this disclosure, further comprising receiving a selection from the plurality of template models, wherein the acquiring is based on the selection.

In combination with any aforementioned methods in this disclosure, the plurality of template models is associated with a symptom type or location.

In combination with any aforementioned methods in this disclosure, the sensory environment includes a user interface for providing a description of the symptom or selecting from a set of predefined descriptions.

In combination with any aforementioned methods in this disclosure, the user interface comprises illustration tools corresponding to a predefined set of symptom characteristics.

In combination with any aforementioned methods in this disclosure, the second digital model is modified to represent changes in qualities of the symptom, including, without limitation, duration, intensity, frequency, depth, topography, sharpness, or appearance.

In combination with any aforementioned methods in this disclosure, the user interface is configured to prompt a user to provide the description of the symptom.

In combination with any aforementioned methods in this disclosure, the prompting comprises presenting a prompt for localizing the symptom on a body of the user.

In combination with any aforementioned methods in this disclosure, the prompting comprises presenting prompts corresponding to a location of the symptom, a size of the symptom or a set of predefined symptom characteristics or qualities.

In combination with any aforementioned methods in this disclosure, the method further comprises modifying the second digital model responsive to user input.

In combination with any aforementioned methods in this disclosure, the method further comprising: receiving current diagnostic data for a user including vital sign data, neuro-imaging data, nociceptor activity data, or central nervous activity (CNS) data; and modifying the second digital model based on the current diagnostic data.

In combination with any aforementioned methods in this disclosure, vital sign data includes heart rate, heart rate variability, galvanic skin response, brain waves, EEG data, blood pressure, breathing rate, diaphoresis, pupil dilation, eye movement, temperature, or facial expression data.

In combination with any aforementioned methods in this disclosure, the sensory environment includes an avatar of a user.

In combination with any aforementioned methods in this disclosure, the avatar represents a body of the user.

In combination with any aforementioned methods in this disclosure, a view of the avatar corresponds to a first-person view or a third-person view for the user.

In combination with any aforementioned methods in this disclosure, the third-person view is a perspective view, a front view, a side view, a back view, a top view, or a bottom view.

In combination with any aforementioned methods in this disclosure, the view of the avatar switches between the first- and third-person views.

In combination with any aforementioned methods in this disclosure, the method further comprises modifying the first digital model to generate a change to the avatar responsive to user input.

In combination with any aforementioned methods in this disclosure, the change is in a position, size, or appearance of the avatar.

In combination with any aforementioned methods in this disclosure, the second or third sensory signals are generated on or within the avatar.

In combination with any aforementioned methods in this disclosure, the first sensory signals are generated in accordance with a localization of the symptom.

In combination with any aforementioned methods in this disclosure, generation of the third sensory signals comprises a passive animation of the symptom.

In combination with any aforementioned methods in this disclosure, the method further comprises determining a symptom alleviation method, wherein creation of the third digital model is based on the symptom alleviation method.

In combination with any aforementioned methods in this disclosure, the symptom alleviation method includes parameters comprising a duration, intensity, manner, or quality of symptom alleviation.

In combination with any aforementioned methods in this disclosure, the third digital model corresponds to one or more of: a reduction in size of, an increase of a distance from; an evaporation of, a recoloring/discoloration of; a dilution of; a diffusion of; a dissipation of; a relocation of; a reduction in frequency of; a distortion of; a disappearing of; a washing or blowing away of; a removal of; a throwing away of; a silencing of; a slowing of; a melting of; a healing of; a stilling of; or a cooling of the symptom.

In combination with any aforementioned methods in this disclosure, the third digital model corresponds to creating a set of stimuli, which leads the user to experience changes in body self-perception or an out-of-body experience.

In combination with any aforementioned methods in this disclosure, the symptom is real or imagined.

In combination with any aforementioned methods in this disclosure, the symptom corresponds to a missing limb.

In combination with any aforementioned methods in this disclosure, the symptom comprises a chronic symptom, an acute symptom, a visceral symptom, or a neuropathic symptom.

In combination with any aforementioned methods in this disclosure, the symptom corresponds to a current physical injury or emotional suffering of a user.

In combination with any aforementioned methods in this disclosure, the method further comprises directing a device to physically stimulate a user while the user is being presented with the sensory environment.

In combination with any aforementioned methods in this disclosure, the method further comprises directing a device to stimulate a muscle of the user while being presented with the sensory environment, wherein the muscle is related to a localization of the symptom or is a trigger for or a factor in experiencing the symptom.

In combination with any aforementioned methods in this disclosure, further comprises directing a device to stimulate an area of a brain of a user while the user is being presented with the sensory environment, wherein the area of the brain is related to the localization of the symptom, a physical, cognitive or emotional experience of the symptom by the user, or a control of the symptom by the user.

In combination with any aforementioned methods in this disclosure, the method further comprises directing a device to entrain a user while being presented with the virtual environment.

In combination with any aforementioned methods in this disclosure, the method further comprises applying a relaxation technique while the patient is being presented with the virtual environment.

In combination with any aforementioned methods in this disclosure, the method further comprises: determining a first symptom response of a user at a first time; determining a second symptom response of the user at a second time; and determining a change in an experience of the symptom by the user by comparing the first symptom response and the second symptom response.

In combination with any aforementioned methods in this disclosure, determining the first or the second symptom response is based on user input or a scan of a target portion of a body of the user.

In combination with any aforementioned methods in this disclosure, the target portion of the body of the user comprises nociceptors or the central nervous system (CNS) or a brain of the user.

In combination with any aforementioned methods in this disclosure, the first time is before the user is presented with the first sensory signals, the second sensory signals or the third sensory signals, and the second time is afterwards.

In combination with any aforementioned methods in this disclosure, the method further comprise: monitoring vital sign data or biometric data of a user; and modifying the second and third digital models responsive to a change in the vital sign or biometric data.

In combination with any aforementioned methods in this disclosure, the method further comprises: generating, before a user is presented with the first sensory signals, the second sensory signals or the third sensory signals, a first map of a range of motion, a strength test, or an endurance test of the user; generating, after the user is presented with the first sensory signals, the second sensory signals or the third sensory signals, a second map of the range of motion, strength test, or endurance test; and determining a change in an experience of the symptom by the user based on comparing the first map and second map.

In combination with any aforementioned methods in this disclosure, the method further comprises sending the first, second, or third digital model to a remote device over a communication network.

In combination with any aforementioned methods in this disclosure, the method further comprises receiving a specification of a symptom alleviation method; generating a simplified version of the first, second, or third digital model, and sending the specification and the simplified version to a remote device over a communication network.

In combination with any aforementioned methods in this disclosure, the third sensory signals creates a sensation within the user of the mind or consciousness of the user leaving the user's body and floating above or beside the user's body, the mind or consciousness moving from one body to another, a part of the body leaving the main body, or one or more symptoms leaving the body.

Preferred embodiments, alone or in combination with any aforementioned methods in this disclosure, include a method of representing symptom alleviation, comprising receiving information regarding alleviating a symptom, including a selection from a plurality of predetermined modes for representing symptom alleviation; generating a digital model for alleviating the symptom based on the received information; and managing a symptom alleviation experience based on the received information.

In combination with any aforementioned methods in this disclosure, the plurality of predetermined modes includes a passive mode, an active mode, and a responsive mode, wherein when the selection is the passive mode, the managing includes sending the digital model to an output device and causing the output device to generate sensory signals based on the digital model, wherein when the selection is the active mode, the managing includes receiving user instructions from an input device, and wherein when the selection is the responsive mode, the managing includes receiving biometric data from a sensor device.

In combination with any aforementioned methods in this disclosure, when the selection is the active or responsive mode, the managing further includes updating the digital mode based on the user instructions or the biometric data.

In combination with any aforementioned methods in this disclosure, when the selection is the active or responsive mode, the managing further includes updating the digital model based on the user instructions or user biofeedback.

In combination with any aforementioned methods in this disclosure, the biofeedback includes a heart rate, heart rate variability, breathing, galvanic skin response, brain waves, EEG signals, fMRI signals, or muscle tension.

In combination with any aforementioned methods in this disclosure, the third digital model includes verbal or visual teachings for the user, including, without limitation, skills for coping with the symptom or affirmations on the user's power to control or alleviate the symptom.

In combination with any aforementioned methods in this disclosure, the method further comprises receiving a specification of a symptom alleviation method; generating a simplified version of the first, second, or third digital model, and sending the specification and the simplified version to a remote device over a communication network.

Preferred embodiments, alone or in combination with any aforementioned methods in this disclosure, include a system for representing symptoms and symptom alleviation, comprising: a processor; and a memory operatively coupled to the processor and configured for storing data instructions that, when executed by the processor, cause the system to perform a method, the method comprising: creating a first digital model for generating a sensory environment comprising first sensory signals; causing an output device to execute the first digital model to generate the sensory environment; creating a second digital model for a symptom, wherein the second digital model causes generation of second sensory signals; causing the output device to generate the second sensory signals within the sensory environment based on the second digital model; creating a third digital model of an alleviation or removal of the symptom based on the first or the second digital models, wherein the third digital model causes generation of third sensory signals, and wherein at least a portion of the second sensory signals and/or third sensory signals change continuously over time to human perception; and causing the output device to generate the third sensory signals within the sensory environment based on the third digital model.

In combination with any aforementioned systems in this disclosure, the first, second, or third device is a head mounted virtual reality display, and augmented reality display, monitor, speaker, haptic device, holographic display, smart wearable device, or a smart handheld device.

In combination with any aforementioned systems in this disclosure, the method further comprises directing a stimulating device to physically stimulate a user while the user is being presented with the sensory environment.

In combination with any aforementioned systems in this disclosure, the stimulating device is a muscle-stimulating device or a brain-stimulating device.

Preferred embodiments, alone or in combination with any aforementioned methods or systems in this disclosure, include a non-transitory computer-readable storage medium with instructions stored thereon that, when executed by a processor, cause the processor to perform a method of representing symptoms and symptom alleviation, the method comprising: creating, by one or more processors, a first digital model for generating a sensory environment comprising first sensory signals; causing an output device to execute the first digital model to generate the sensory environment; creating a second digital model for a symptom, wherein the second digital model causes generation of second sensory signals; causing the output device to generate the second sensory signals within the sensory environment based on the second digital model; creating a third digital model of an alleviation or removal of the symptom based on the first or the second digital models, wherein the third digital model causes generation of third sensory signals, and wherein at least a portion of the second sensory signals and/or third sensory signals change continuously over time to human perception; and causing the output device to generate the third sensory signals within the sensory environment based on the third digital model.

The invention claimed is:
1. A system for modeling a symptom of a user, comprising:
a display system;
a sensory device configured to produce one or more of audio, tactile, olfactory, or thermal signals; and
a computer system communicatively coupled with the display system and the sensory device, the computer system comprising one or more processors and one or more computer-readable storage media having stored thereon computer-executable instructions that, when executed by the one or more processors, configure the computer system to perform at least the following:
generate a multidimensional sensory environment configured to provide sensory signals associated with a symptom of a user;
receive, based on user input, a description of the symptom, the description providing values for visual, audio, tactile, olfactory, and/or thermal signals associated with the symptom;
based on the received description of the symptom, generate a symptom digital model comprising (i) a set of visual sensory signals and (ii) a set of one or more of audio, tactile, olfactory, or thermal signals;
cause the display system to produce the set of visual sensory signals associated with the symptom digital model within the multidimensional sensory environment; and
cause the sensory device to output the set of one or more of audio, tactile, olfactory, or thermal signals associated with the symptom digital model,
wherein the set of visual sensory signals and the set of one or more of audio, tactile, olfactory, or thermal signals are associated with each other to both represent the symptom within the multidimensional sensory environment.

2. The system of claim 1, wherein the display system comprises a holographic projector or display and the set of visual sensory signals comprises holographic projections or displays of the digital model, or wherein the display system is configured to produce one or more of augmented reality, virtual reality, or mixed reality display or projection of the digital model.

3. The system of claim 1, wherein the digital model is configured to provide a representation of the user corresponding to a mirror image of the user or wherein the digital model is configured to provide a first-person view or third-person view for the user.

4. The system of claim 1, wherein the sensory device comprises a haptic device and the symptom digital model comprises a set of tactile signals, wherein causing the sensory device to output the symptom digital model comprises causing the haptic device to produce the set of haptic signals associated with the symptom.

5. The system of claim 4, wherein the computer-executable instructions, when executed by the one or more processors, further cause the computer system to modulate at least one of an intensity, a location, or a frequency of the set of tactile signals to correspond with a representation of symptom alleviation.

6. The system of claim 5, wherein the intensity, the location, or the frequency of the set of tactile signals is modulated to correspond with data received from a biofeedback device.

7. The system of claim 1, wherein the digital model represents the symptom as an abstraction or metaphor.

8. The system of claim 1, wherein the sensory device comprises an olfactory device and the symptom digital model comprises a set of olfactory signals such that causing the sensory device to output the symptom digital model comprises causing the olfactory device to produce the set of olfactory signals associated with the symptom.

9. The system of claim 8, wherein the computer-executable instructions, when executed by the one or more processors, further cause the computer system to modulate at least one of an intensity, a duration, or a fragrance of the set of olfactory signals to correspond with a representation of symptom alleviation.

10. The system of claim 1, wherein the sensory device comprises a heating or cooling device, and wherein the symptom digital model comprises a set of thermal signals such that causing the sensory device to output the symptom digital model comprises causing the heating or cooling device to produce the thermal signals associated with the symptom.

11. The system of claim 10, wherein the computer-executable instructions, when executed by the one or more processors, further cause the computer system to modulate at least one of an intensity, a duration, or a location of the set of thermal signals to correspond with a representation of symptom alleviation.

12. The system of claim 1, wherein the computer system is associated with a mobile device.

13. The system of claim 1, wherein the computer-executable instructions, when executed by the one or more processors, further cause the computer system to modulate one or more of the visual, audio, tactile, olfactory, or thermal signals within the multidimensional sensory environment in a manner that represents lessening or alleviation of the symptom of the digital model.

14. A computer program product comprising one or more hardware storage devices having stored thereon one or more computer-executable instructions that are executable by one or more processors of a computer system to cause the computer system to perform at least the following:
   generate a multidimensional sensory environment using a display system and sensory device configured to produce one or more of audio, tactile, olfactory, or thermal signals, the multidimensional sensory environment configured to provide sensory signals associated with a symptom of a user;
   receive, based on user input, a selection of the symptom or a description of the symptom, the selection or description providing values for visual, audio, tactile, olfactory, and/or thermal signals associated with the symptom;
   based on the received selection or description of the symptom, generate a symptom digital model comprising (i) a set of visual sensory signals and (ii) a set of one or more of audio, tactile, olfactory, or thermal signals;
   cause the display system to produce the set of visual sensory signals associated with the symptom digital model within the multidimensional sensory environment; and
   cause the sensory device to output the set of one or more of audio, tactile, olfactory, or thermal signals associated with the symptom digital model,
   wherein the set of visual sensory signals and the set of one or more of audio, tactile, olfactory, or thermal signals are associated with each other to both represent the symptom within the multidimensional sensory environment.

15. The computer program product of claim 14, wherein the computer-executable instructions are further configured to, when executed, cause the computer system to change one or more of the visual, audio, tactile, olfactory, or thermal signals within the multidimensional sensory environment in a manner that represents improvement of the symptom, lessening of the symptom, or alleviation of the symptom.

16. A system for modeling a symptom of a user, comprising:
   a display system;
   a sensory device configured to produce one or more of audio, tactile, olfactory, or thermal signals; and
   a computer system communicatively coupled with the display system and the sensory device, the computer system comprising one or more processors and one or more computer-readable storage media having stored thereon computer-executable instructions that, when executed by the one or more processors, configure the computer system to perform at least the following:
   generate a multidimensional sensory environment configured to provide sensory signals to the user;
   receive user input, wherein the user selects a symptom from a template, the selected symptom being associated with values for visual, audio, tactile, olfactory, and/or thermal signals associated with the symptom;
   based on the selected symptom, generate a symptom digital model comprising (i) a set of visual sensory signals and (ii) a set of one or more of audio, tactile, olfactory, or thermal signals;
   cause the display system to produce the set of visual sensory signals associated with the symptom digital model within the multidimensional sensory environment;
   cause the sensory device to output the set of one or more of audio, tactile, olfactory, or thermal signals associated with the symptom digital model, wherein the set of visual sensory signals and the set of one or more of audio, tactile, olfactory, or thermal signals are associated with each other to both represent the symptom within the multidimensional sensory environment; and change one or more of the visual, audio, tactile, olfactory, or thermal signals within the multidimensional sensory environment in a manner that represents an improvement of the symptom, a lessening of the symptom, or an alleviation of the symptom.

17. The system of claim 16, wherein the template is developed by generalizing symptom input from other users.

18. The system of claim 16, wherein the sensory device comprises one or more of a haptic device, olfactory device, or heating/cooling device, and the symptom digital model comprises one or more of tactile signals, olfactory signals, or thermal signals, wherein causing the sensory device to output the symptom digital model comprises causing one or more of:
- the haptic device to produce the set of haptic signals associated with the symptom;
- the olfactory device to produce the set of olfactory signals associated with the symptom; or
- the heating/cooling device to produce the set of thermal signals associated with the symptom.

19. The system of claim 18, wherein the computer-executable instructions, when executed by the one or more processors, further cause the computer system to modulate at least one of:
- an intensity, a location, or a frequency of the set of tactile signals to correspond with a representation of symptom alleviation;
- an intensity, a duration, or a fragrance of the set of olfactory signals to correspond with a representation of symptom alleviation; or
- an intensity, a duration, or a location of the set of thermal signals to correspond with a representation of symptom alleviation.

20. A system for modeling a symptom of a user, comprising:
- a display system;
- a sensory device configured to produce one or more of audio, tactile, olfactory, or thermal signals; and
- a computer system communicatively coupled with the display system and the sensory device, the computer system comprising one or more processors and one or more computer-readable storage media having stored thereon computer-executable instructions that, when executed by the one or more processors, configure the computer system to perform at least the following:
- generate a multidimensional sensory environment configured to provide sensory signals associated with a symptom of a user;
- receive, based on user input, a description of the symptom, the description providing values for visual, audio, tactile, olfactory, and/or thermal signals associated with the symptom;
- based on the received description of the symptom, generate a symptom digital model comprising (i) a set of visual sensory signals and (ii) a set of one or more of audio, tactile, olfactory, or thermal signals;
- cause the display system to produce the set of visual sensory signals associated with the symptom digital model within the multidimensional sensory environment; and
- cause the sensory device to output the set of one or more of audio, tactile, olfactory, or thermal signals associated with the symptom digital model,
- wherein the symptom digital model is configured to change in association with movement of the user such that an intensity, location, and/or frequency of one or more of the sensory signals is modulated in association with user movement.

21. The system of claim 20, wherein the symptom digital model is configured such that an intensity, location, and/or frequency of one or more of the sensory signals increases as the user extends a movement toward a limit in range of motion.

22. The system of claim 21, wherein the symptom digital model adjusts over repeated attempts of a particular movement of the user to provide progressive movement therapy to the user with respect to the particular movement.

* * * * *